United States Patent
Ho et al.

(10) Patent No.: US 7,357,136 B2
(45) Date of Patent: Apr. 15, 2008

(54) PATIENT INTERFACE ASSEMBLY AND SYSTEM USING SAME

(75) Inventors: Peter Ho, Pittsburgh, PA (US); Jerome Matula, Apollo, PA (US); Richard J. Lordo, Butler, PA (US); Lance Busch, Trafford, PA (US); Derrik Andrews, Markleton, PA (US); Luke Stonis, Columbus, OH (US); Chris Von Dolhen, St. Louis Park, MN (US)

(73) Assignee: RIC Investments, LLC, Wilmington, DE (US)

( * ) Notice: Subject to any disclaimer, the term of this patent is extended or adjusted under 35 U.S.C. 154(b) by 142 days.

(21) Appl. No.: 10/918,832

(22) Filed: Aug. 13, 2004

(65) Prior Publication Data

US 2005/0076913 A1     Apr. 14, 2005

Related U.S. Application Data

(60) Provisional application No. 60/496,059, filed on Aug. 18, 2003.

(51) Int. Cl.
*A61M 16/06* (2006.01)
*A62B 18/08* (2006.01)

(52) U.S. Cl. .............................. 128/207.11; 128/207.13; 128/206.11

(58) Field of Classification Search ........... 128/207.11, 128/207.18, 204.11, 204.12, 204.24, 204.25, 128/205.11, 205.25, 206.11, 206.18, 207.13, 128/200.24, 200.29, 201.11, 201.27, 202.27, 128/204.18, 206.27, 207.17, 911, 912, DIG. 26
See application file for complete search history.

(56) References Cited

U.S. PATENT DOCUMENTS 853,439 A * 5/1907 Clark .................... 128/207.18
1,081,745 A   12/1913 Johnston et al.

(Continued)

FOREIGN PATENT DOCUMENTS

| WO | WO 00/74758 A1 | 12/2000 |
| WO | WO 01/00266 A2 | 1/2001 |
| WO | WO 02/096342 A2 | 12/2002 |

OTHER PUBLICATIONS

Website, "Breeze DreamSeal", 1 page, Dec. 11, 2003.

(Continued)

*Primary Examiner*—Teena Mitchell
*Assistant Examiner*—Shumaya B. Ali
(74) *Attorney, Agent, or Firm*—Michael W. Haas

(57) ABSTRACT

A patient interface assembly that includes a patient interface device, a headgear, and coupling member joining the interface device to a headgear. In one embodiment, a spring biases the interface device against the face during use. In a further embodiment, the patient interface device is a nasal cushion having a formable support mounted to the nasal cushion for providing support and adjustment of the nasal cushion to improve fit and comfort. The headgear assembly in one embodiment is a semi-rigid, minimal contact harness and includes an adjustment assembly that allows for a simultaneous adjustment of multiple straps. An adjustment assembly on the headgear provides a gross adjustment of the position of the interface relative to the patient and a biasing force to urge the patient interface device against the patient's face. In a further embodiment, a pair of rigid connecting members couple the patient interface device to the headgear.

10 Claims, 25 Drawing Sheets

U.S. PATENT DOCUMENTS

| | | | |
|---|---|---|---|
| 1,323,217 A | 11/1919 | Darrow | |
| 2,259,817 A | 10/1941 | Hawkins | |
| 2,818,067 A * | 12/1957 | Rebikoff et al. | 128/201.11 |
| 3,978,854 A | 9/1976 | Mills, Jr. | |
| 4,354,488 A | 10/1982 | Bartos | |
| 4,367,735 A | 1/1983 | Dali | |
| 4,782,832 A | 11/1988 | Trimble et al. | |
| 4,808,160 A * | 2/1989 | Timmons et al. | 604/94.01 |
| 4,919,128 A | 4/1990 | Kopala et al. | |
| 4,938,209 A | 7/1990 | Fry | |
| 5,042,478 A | 8/1991 | Kopala et al. | |
| 5,069,205 A * | 12/1991 | Urso | 128/201.24 |
| 5,181,507 A * | 1/1993 | Michel et al. | 128/201.25 |
| 5,269,296 A | 12/1993 | Landis | |
| 5,477,852 A | 12/1995 | Landis et al. | |
| 5,517,986 A | 5/1996 | Starr et al. | |
| 5,533,506 A | 7/1996 | Wood | |
| 5,538,000 A | 7/1996 | Rudolph | |
| 5,558,089 A | 9/1996 | Castiglione | |
| 5,724,965 A | 3/1998 | Handke et al. | |
| 5,752,510 A | 5/1998 | Goldstein | |
| 5,921,239 A | 7/1999 | McCall et al. | |
| 6,012,455 A | 1/2000 | Goldstein | |
| 6,019,101 A | 2/2000 | Cotner et al. | |
| 6,119,693 A * | 9/2000 | Kwok et al. | 128/207.11 |
| 6,119,694 A | 9/2000 | Correa et al. | |
| 6,347,631 B1 | 2/2002 | Hansen et al. | |
| 6,431,172 B1 | 8/2002 | Bordewick | |
| 6,463,931 B1 | 10/2002 | Kwok et al. | |
| 6,497,232 B2 | 12/2002 | Fecteau et al. | |
| 6,516,802 B2 | 2/2003 | Hansen et al. | |
| 6,520,182 B1 * | 2/2003 | Gunaratnam | 128/206.27 |
| 6,532,961 B1 * | 3/2003 | Kwok et al. | 128/206.21 |
| 6,561,191 B1 | 5/2003 | Kwok | |
| 6,581,594 B1 * | 6/2003 | Drew et al. | 128/204.18 |
| 6,595,214 B1 | 7/2003 | Hecker et al. | |
| 6,662,803 B2 * | 12/2003 | Gradon et al. | 128/205.25 |
| 6,712,072 B1 | 3/2004 | Lang | |
| 6,851,428 B2 * | 2/2005 | Dennis | 128/205.25 |
| 6,854,465 B2 * | 2/2005 | Bordewick et al. | 128/207.11 |
| 2002/0104540 A1 * | 8/2002 | Kwok et al. | 128/205.25 |
| 2003/0075180 A1 | 4/2003 | Raje et al. | |

OTHER PUBLICATIONS

Website, "ADAM Circuit (nasal pillows)", 3 pages, Dec. 11, 2003.

* cited by examiner

PATIENT INTERFACE ASSEMBLY AND SYSTEM USING SAME

CROSS-REFERENCE TO RELATED APPLICATIONS

This application claims priority under 35 U.S.C. § 119(e) from provisional U.S. patent application No. 60/496,059, filed Aug. 18, 2003, the contents of which are incorporated herein by reference.

BACKGROUND OF THE INVENTION

1. Field of the Invention

The present invention pertains to a patient interface assembly, a system for supplying a flow of gas to a patient that incorporates such an assembly, and to a patient interface device and a headgear for use in such an assembly.

2. Description of the Related Art

There are numerous situations where it is necessary or desirable to deliver a flow of breathing gas, non-invasively, to the airway of a patient, i.e., without intubating the patient or surgically inserting a tracheostomy tube in their trachea. For example, it is known to ventilate a patient using a technique known as non-invasive ventilation. It is also known to deliver continuous positive airway pressure (CPAP) or variable airway pressure, which varies with the patient's respiratory cycle or a monitored condition of the patient, to treat a medical disorder, such as sleep apnea syndrome, in particular, obstructive sleep apnea (OSA), congestive heart failure, stroke, Cheynes-Stokes respiration, etc. Non-invasive ventilation and pressure support therapies involve the placement of a patient interface device, which is typically a nasal or nasal/oral mask, on the face of patient to interface the ventilator or pressure support device with the airway of the patient, so that a flow of breathing gas can be delivered from the pressure/flow generating device to the airway of the patient.

Because such patient interface devices are typically worn for an extended period of time, a variety of concerns must be taken into consideration. For example, in providing CPAP or other positive pressure therapy to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy.

Typically patient interface devices include a mask shell having a cushion attached to the shell that contacts the surface of the patient. The mask shell and cushion are held in place by a headgear that wraps around the head of the patent. The mask and headgear form the patient interface assembly. A typical headgear includes flexible, adjustable straps that extend from the mask to attach the mask to the patient. Other techniques for attaching a patient interface device use a vice-like device that anchors at the front and back of the patient's head to support the mask on the user. See, e.g., U.S. Pat. No. 6,516,802. While such conventional interface devices are generally well accepted, there remains a class of patients that do not find these devices to be sufficiently comfortable, too bulky, or otherwise inadequate. Thus, alternative techniques for interfacing a pressure support system to the airway of a patient are desired.

SUMMARY OF THE INVENTION

Accordingly, the present invention provides a patient interface assembly that addresses the above-identified concerns and that overcomes shortcomings of conventional patient interface assemblies. The patient interface assembly of the present invention provides the patient with improved patient interface stability and overall comfort. The present invention further provides a system for delivering a flow of gas to a patient that addresses the above identified concerns and that does not suffer from the shortcomings of conventional techniques. This is achieved by providing a system for delivering a flow of gas to a patient that includes a gas flow generating device capable of producing a flow of gas and a conduit having a first end portion operatively coupled to the gas flow generating device and a second end portion. The conduit carries the flow of gas from the gas flow generating device. The system includes a patient interface assembly comprising a patient interface device operatively coupled to the second end portion of the conduit and a headgear.

The patient interface device, in one embodiment of the present invention, is a nasal interface device having a nasal cushion and a pair of laterally spaced nares elements for insertion into the nostrils of the patient. A formable support is preferably mounted to the nasal cushion for providing support for the nasal cushion while allowing for adjustments to provide increased fit and comfort of the nasal cushion. The nasal cushion is coupled to a coupling elbow or cradle having exhaust diffusion plates.

The headgear assembly of the present invention includes a substantially rigid, minimal contact harness assembly. The headgear of an exemplary embodiment includes an adjustment assembly that allows for a simultaneous adjustment of multiple straps.

A length adjustment assembly in one embodiment adjusts the distance between an adjustment assembly and the nasal interface device to accommodate patients having different facial sizes. The adjustment assembly is a position adjustment mechanism which provides a force adjustment by an integrated spring. The adjustment assembly allows a cantilevered support to support the patient interface device without a set of headgear straps located at the patient interface device.

In a further embodiment, the coupling member couples the patient interface device to the headgear and a spring, associated with the coupling member, biases the patient interface device against such a patient's face when the patient interface assembly being donned by such a patient. This ensures that the patient interface device is properly seated on the user.

In yet another embodiment, a rigid coupling member couples the patient interface device to the headgear. The rigid coupling member includes a first rigid arm connected between a first side of the patient interface device and a first side of the headgear and a second rigid arm connected between a second side of the patient interface device and a second side of the headgear. Preferably the length of the first and second arms is adjustable to properly fit the patient interface assembly on the patient.

These and other features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
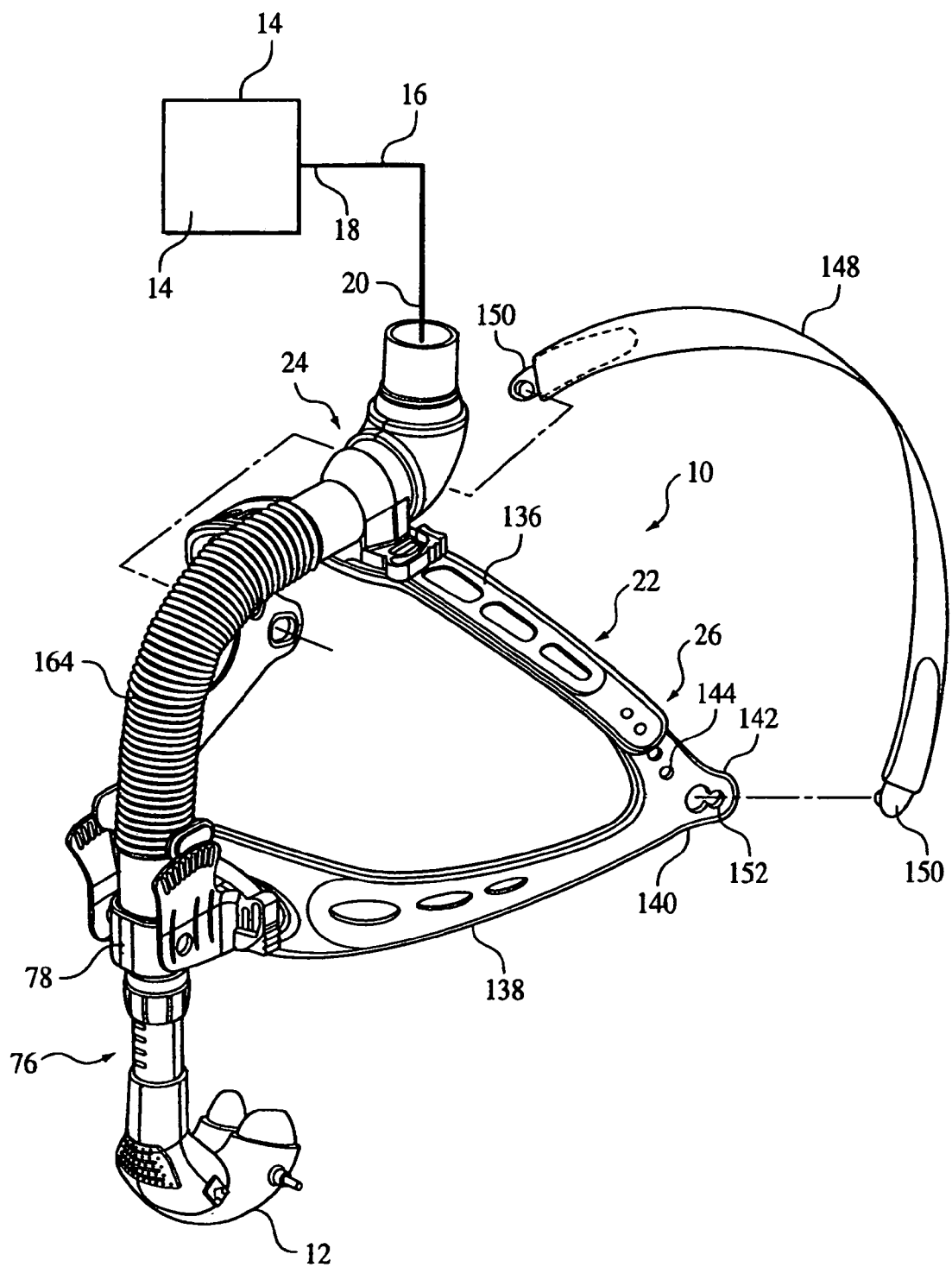
FIG. 1 is a side perspective view of a patient interface assembly according to the principles of the present invention.
Figure 2:
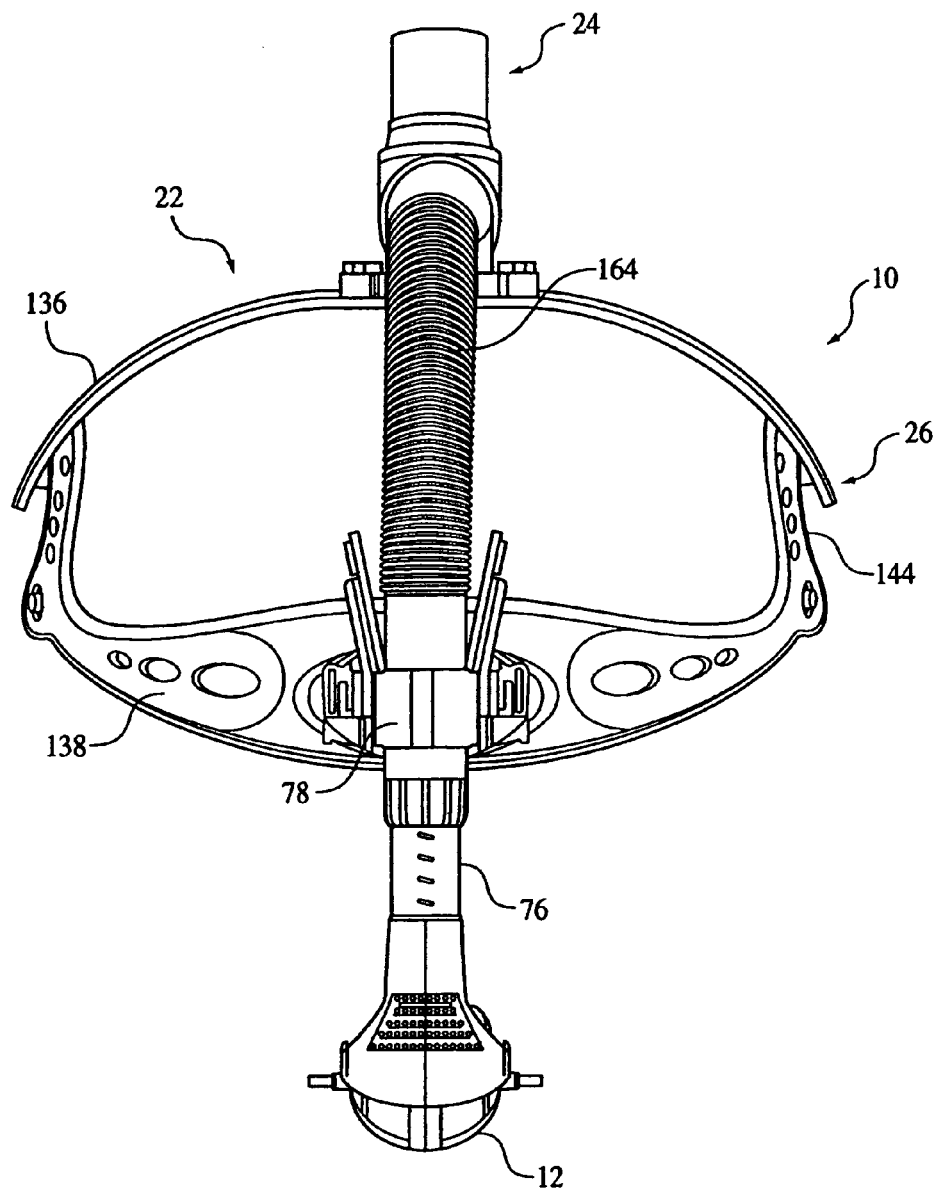
FIG. 2 is a front view of the patient interface assembly of FIG. 1.
Figure 4:
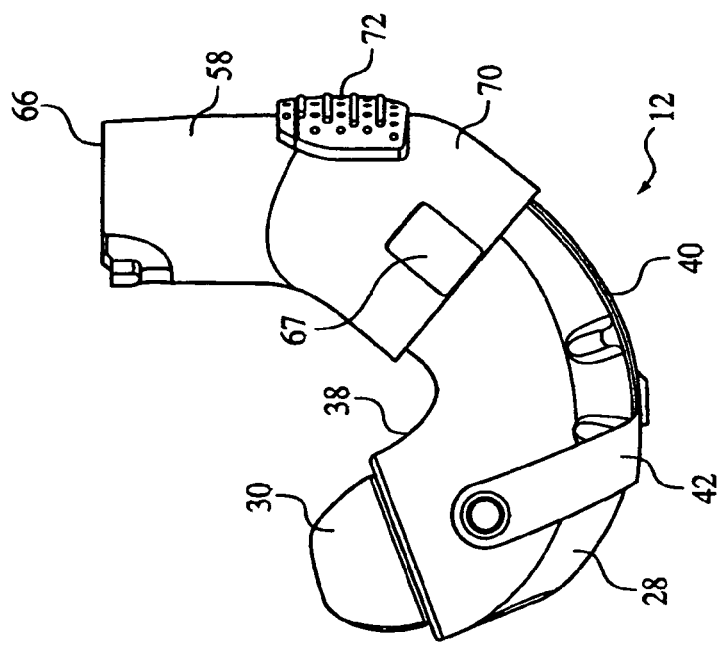
FIG. 4 is a side view of the nasal interface device and cradle of FIG. 3.
Figure 3:
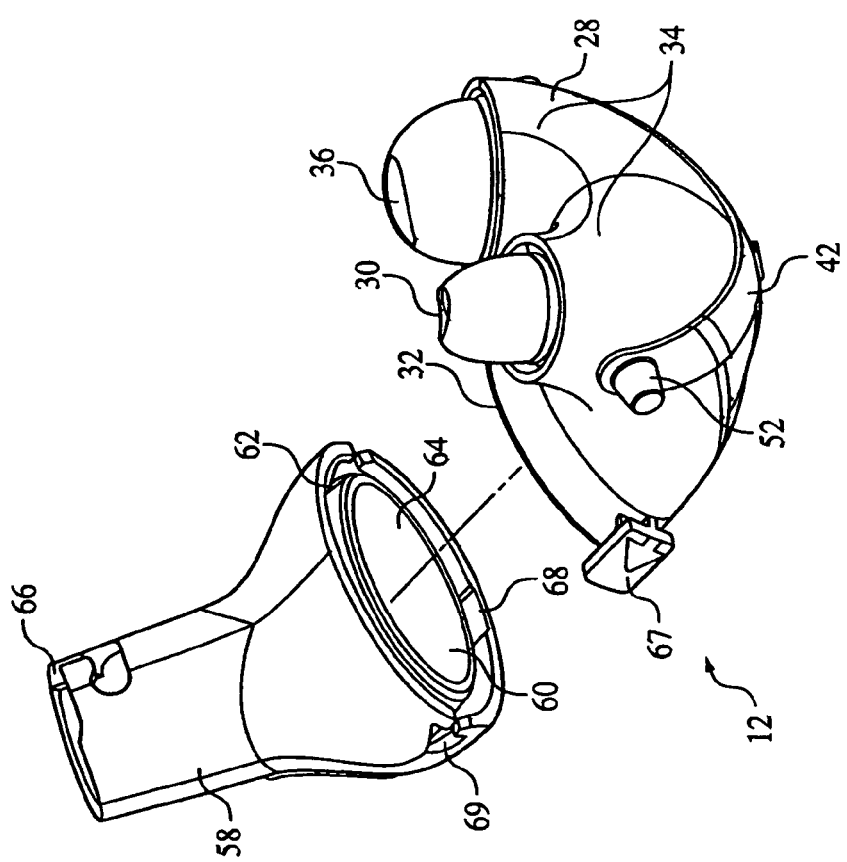
FIG. 3 is an exploded view of a nasal interface device and cradle in the patient interface assembly of FIG. 1.
Figure 5:
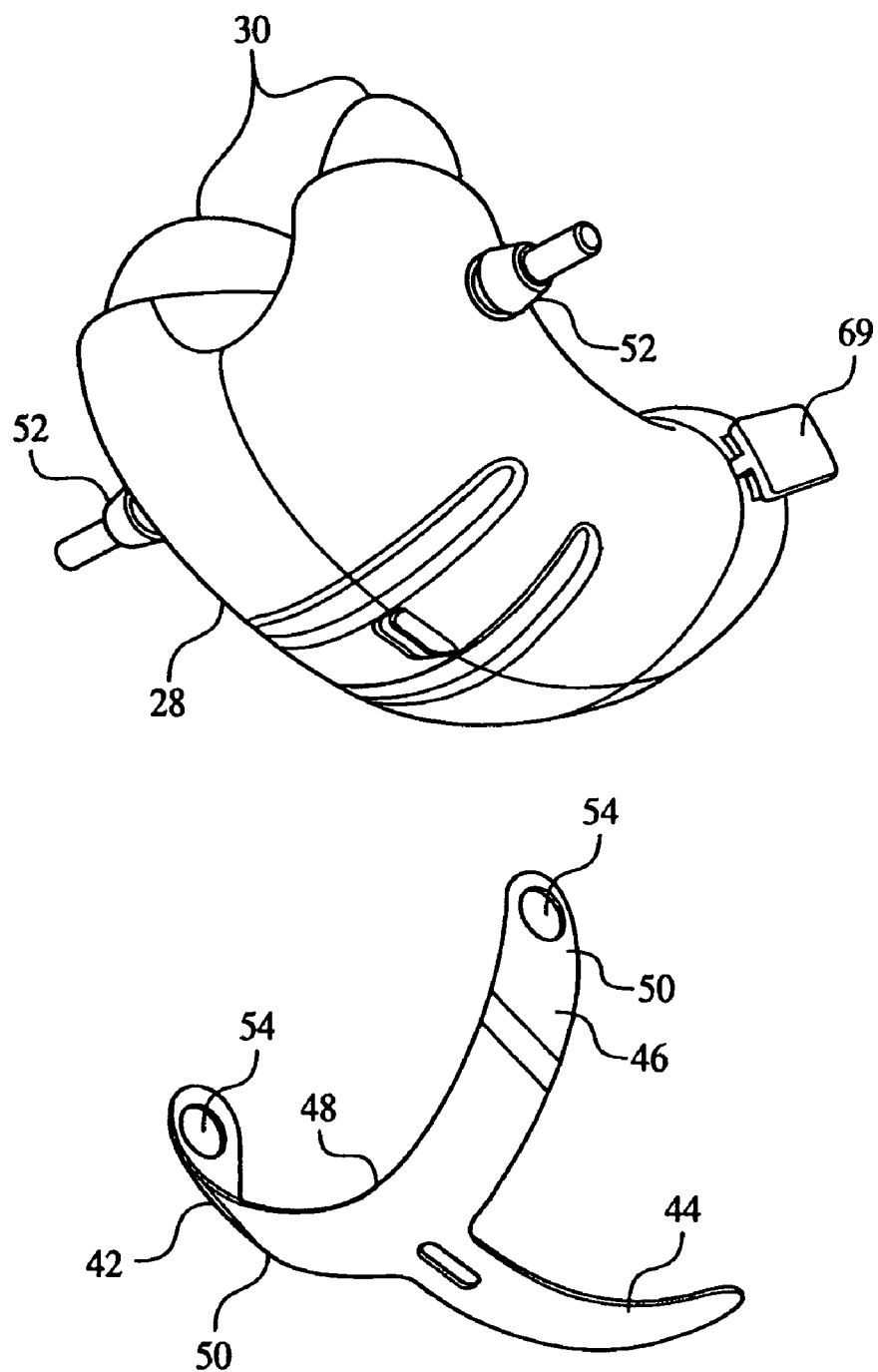
FIG. 5 is an exploded view of the nasal interface device and formable support in the patient interface assembly of FIG. 1.
Figure 6:
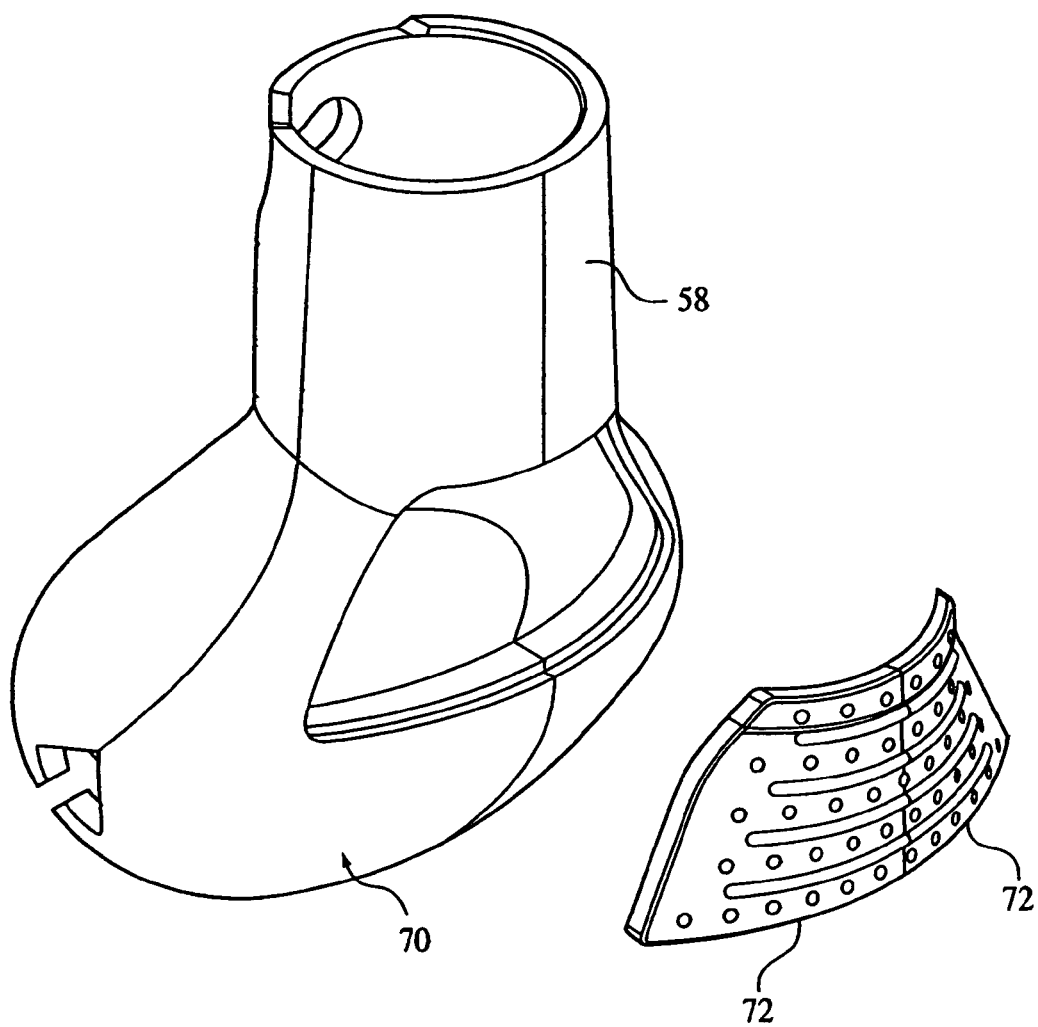
FIG. 6 is an exploded view of the cradle and an exhaust diffusion plate adapted to be disposed on the cradle in the patient interface assembly of FIG. 1.
Figure 7:
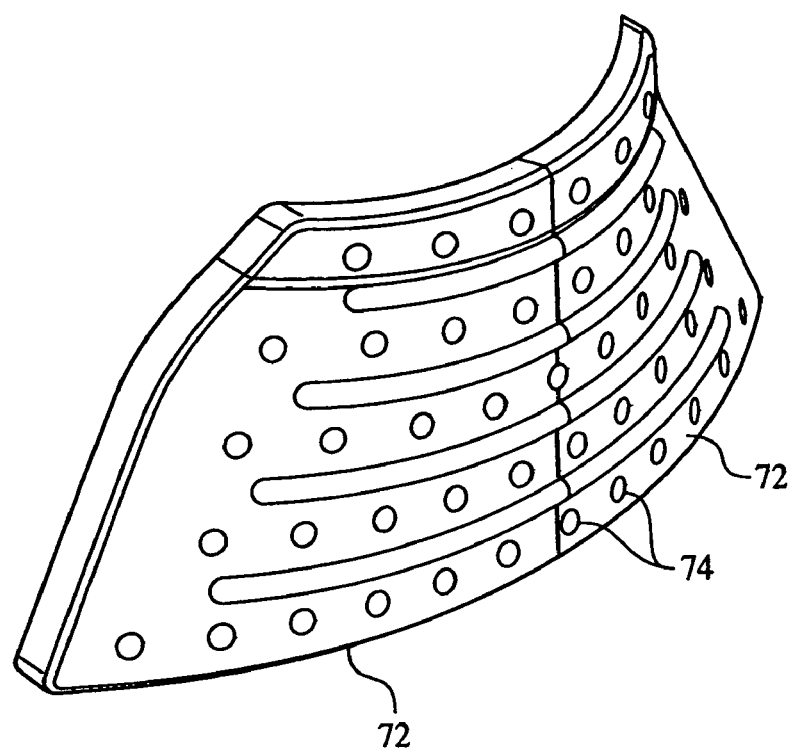
FIG. 7 is a perspective view of the exhaust diffusion plate of FIG. 6.
Figure 8:
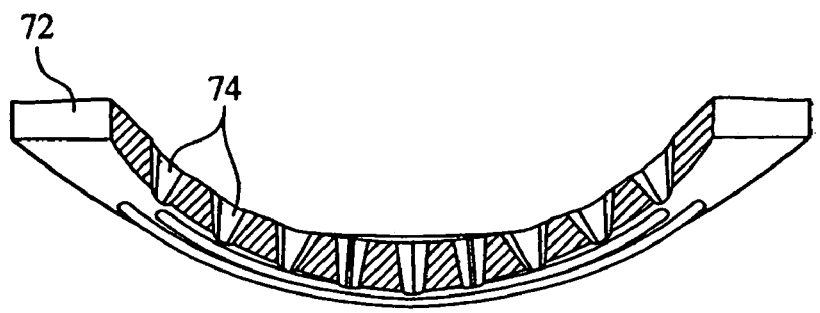
FIG. 8 is a cross-sectional view of the exhaust diffusion plate of FIG. 7.
Figure 9:
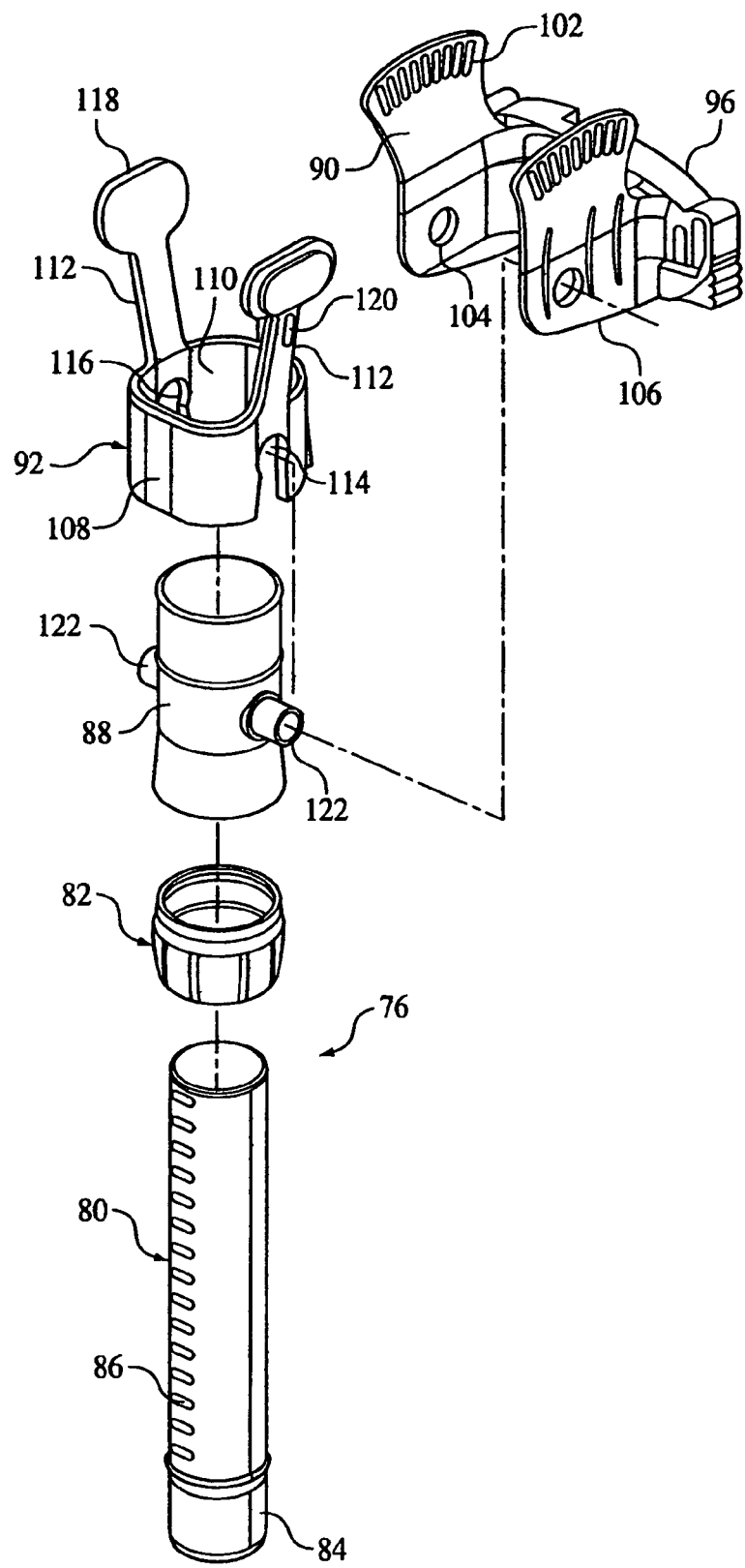
FIG. 9 is an exploded view of a length adjustment assembly and an angle adjustment assembly provided in the patient interface assembly of FIG. 1.
Figure 10:
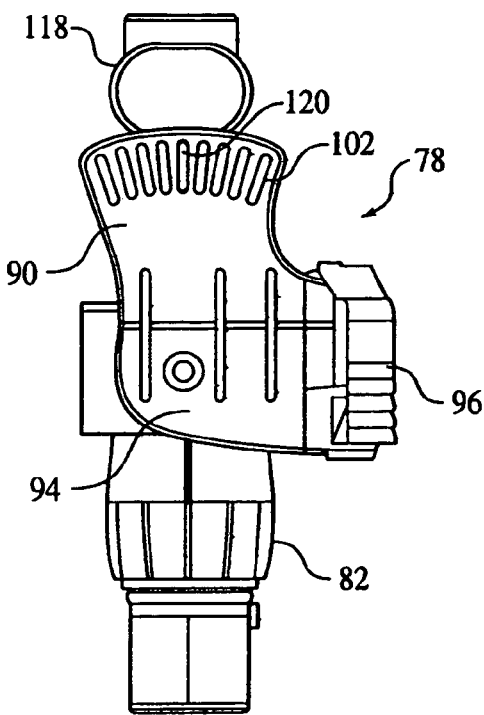
FIG. 10 is a side view of the length adjustment assembly and the angle adjustment assembly of FIG. 9.

FIGS. 1-16 illustrate an exemplary embodiment of a patient interface assembly 10 according to the principles of the present invention. The patient interface assembly 10 supports a patient interface device 12 on a patient's head. Patient interface device 12 communicates a flow of breathing gas between the patient's airway and a pressure generating device 14, such as a ventilator, CPAP device, or variable pressure device, e.g., a BiPAP® device manufactured and distributed by Respironics, Inc. of Pittsburgh, Pa., or an auto-titration pressure support system. A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure generating device 14 is also referred to as a gas flow generating device, because flow results when a pressure gradient is generated.

Communicating a flow of breathing gas between the patient's airway and a pressure generating device 14 includes delivering a flow of breathing gas to the patient from the pressure generating device and exhausting a flow of gas from the patient to ambient atmosphere.

The system for delivering a breathing gas to a patient according to the present invention comprises a pressure or gas flow generating device 14 that produces a flow of gas, a conduit 16, which is also referred to as a patient circuit, having a first end portion 18 operatively coupled to the gas flow generating device and a second end portion 20. Conduit 16 carries the flow of gas from pressure generating device 14 during operation of the system to patient interface device 12 coupled to second end portion 20 of conduit 16. A headgear 22 according to the principles of the present invention, includes a mounting assembly 24 that couples patient interface device 12 to conduit 16, and an adjustable harness assembly 26.

In the illustrated embodiment the patient interface device 12 is a nasal interface device. However, the present invention also contemplates that other devices for communicating a flow of gas to an airway of a patient, such as a nasal mask, oral mask, or mouthpiece, or combination nasal/oral masks, are suitable for use as patient interface device 12.

Patient interface device 12 is generally a nasal interface having a nasal cushion 28 and a pair of laterally spaced nares elements 30 at its distal end for insertion into the nostrils of the patient. See FIGS. 3-4. The body of nasal cushion 28 includes a hollow chamber and extends from an oval shaped opening 32 to laterally spaced outlet legs 34. Each outlet leg 34 is provided with one of nares element 30. The body of nasal cushion 28 curves about an axis substantially perpendicular to a plane separating the two nares elements. Each nares element 30 has an opening 36 to communicate with the nasal passages of the patient. Each of nares elements 30 is substantially dome-shaped having an elliptical base proportional to anthropometrical data of a nostril opening. Nasal cushion 28 is preferably formed from a soft cushiony material, such as silicone, appropriately soft thermoplastic elastomers, closed cell foam, or thin materials.

The curved surface of nasal cushion 28 includes an inner curved surface 38 and an outer curved surface 40 substantially concentric to inner curved surface 38. See FIG. 4. A formable support 42 is preferably mounted to outer curved surface 40. Formable support 42 provides support to nasal cushion 28 while allowing for adjustments to provide increased fit and comfort of the nasal cushion. In the illustrated embodiment, formable support 42 is substantially T-shaped having a stem portion 44 and a cross portion 46. See FIG. 5. Cross portion 46 extends from one end of stem portion 44 at a cross portion midpoint 48. Ends 50 of cross portion 46 curve from midpoint 48.

In the illustrated embodiment, outer curved surface 40 of nasal cushion 28 includes mounting tabs 52 to mount to ends 50 of cross portion 46 of support 42. Ends 50 of the cross portion 46 have through-holes 54 to mount to the corresponding mounting tabs 52. See FIG. 5.

Formable support 42 is preferably formed from a formable metal, such as aluminum. Support 42 can be conformed by pressing on the support with the patient's or caregiver's fingers. By manipulating the support, the angle of the nasal cushion with respect to the facial-frontal plane, and/or the angle of nare contact of the nares elements can be changed.

Alternatively, formable support 42 could be formed from Nitinol (Nickel Titanium Naval Ordinance Laboratory), which is known as shape memory metal, or a plastic with a low softening point temperature, such as EVA (Ethylene Vinyl Acetate) could be used. EVA is commonly used in boil and bite mouthpieces that athletes use. The EVA support in this case could be warmed in hot water and then formed.

Figure 18:
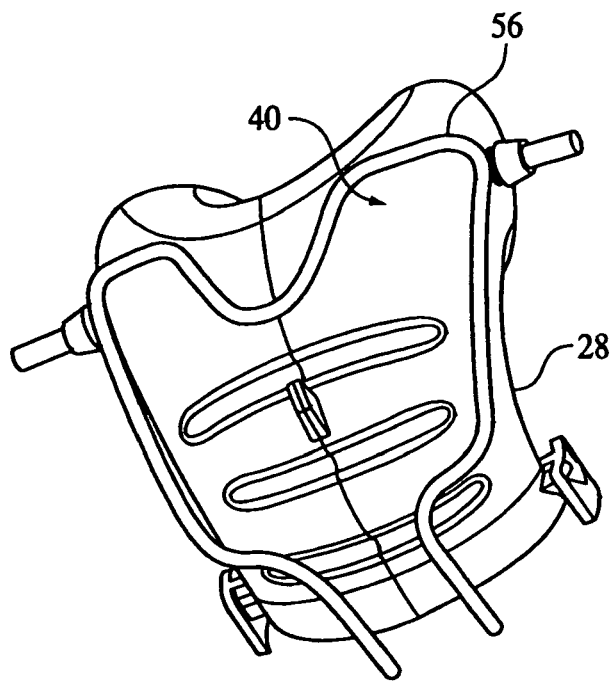
FIG. 18 is a perspective view of a nasal interface device and an alternate embodiment for the formable support.
Figure 19A:
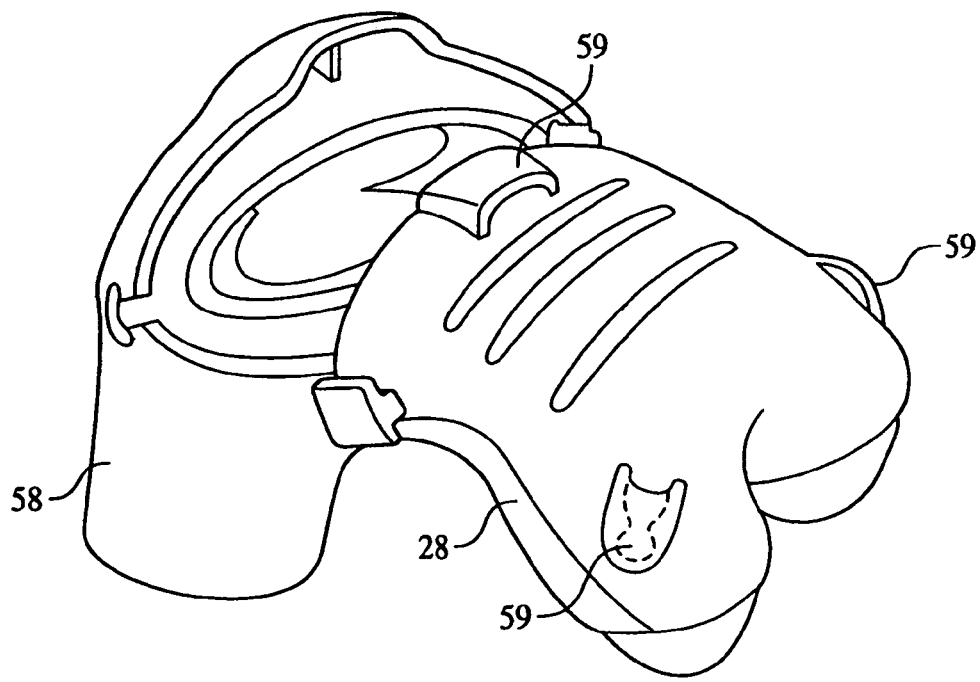
FIG. 19A shows an exploded view of a nasal interface device and cradle according to another alternate embodiment.

While the illustrated formable support 42 is T-shaped, alternatively, the support could be Y-shaped. T or Y-shaped supports 42 can be hollow or solid. While the illustrated embodiments show externally mounted supports, the supports could also be molded within the nasal cushion itself. Alternatively, formable support 42 could be bonded to the cushion in discreet locations. An alternate shaped formable support 56 is illustrated in FIG. 19A. In the embodiment of FIG. 18, support 56 is formed from a formable wire generally following the outline of outer curved surface 40 of nasal cushion 28. By having formable support 56 connected to nasal cushion 28 at discreet locations, there is some relative movement between nasal cushion 28 and support 56 during adjustment of the support.

Figure 19B:
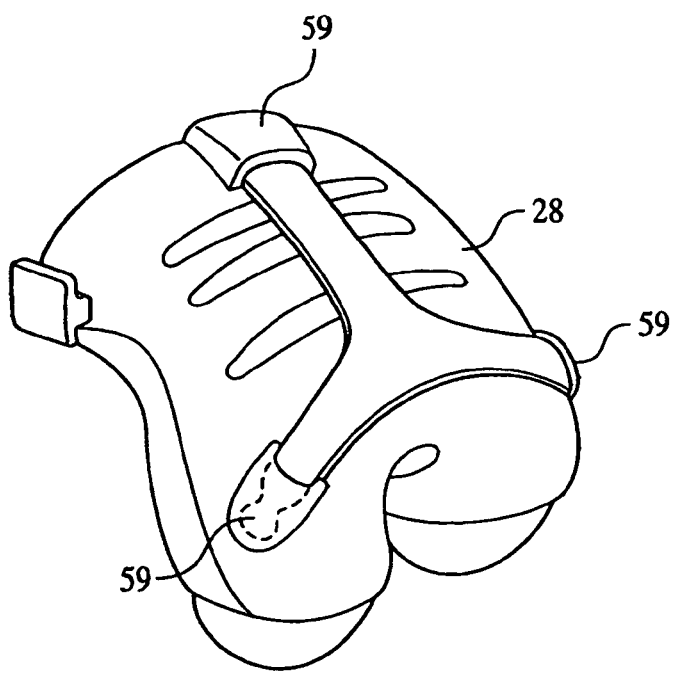
FIG. 19B shows a perspective view of a nasal cushion and support according to the embodiment of FIG. 19A.
Figure 21A:
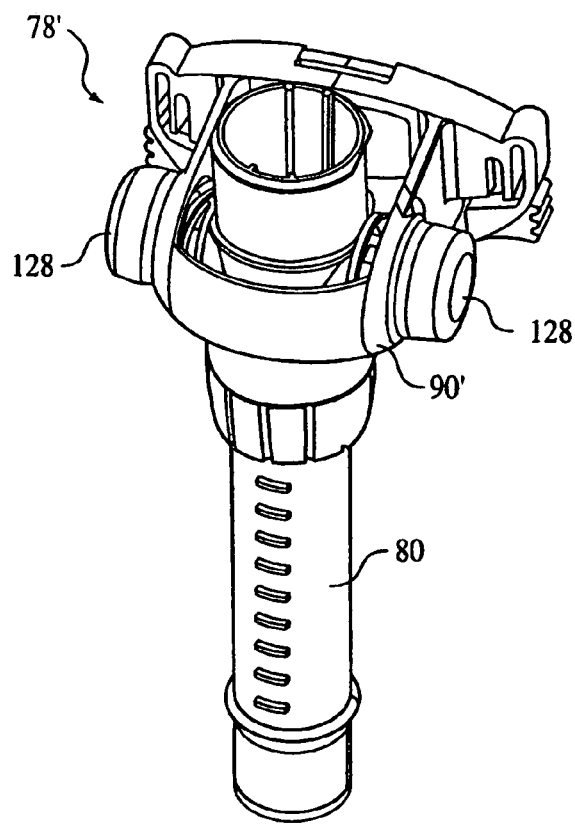
FIG. 21A is a perspective view of an alternate embodiment for the length adjustment assembly and the angle adjustment assembly.
Figure 21B:
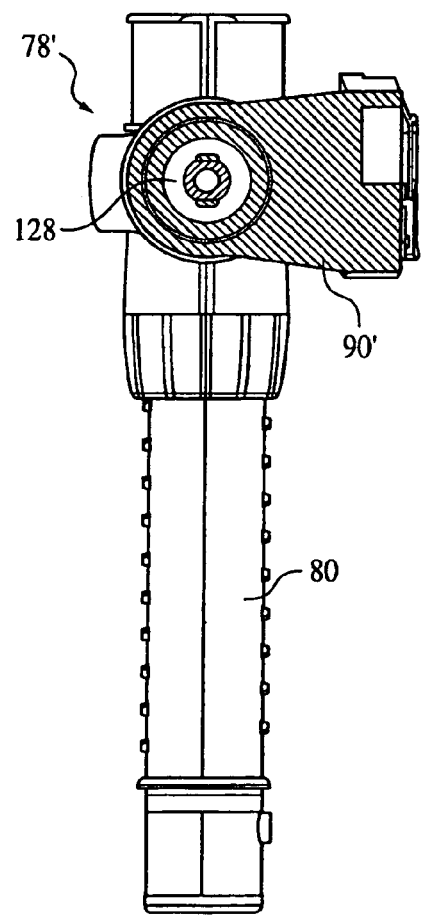
FIG. 21B is a side view of the length adjustment assembly and the angle adjustment assembly of FIG. 21A.
Figure 21C:
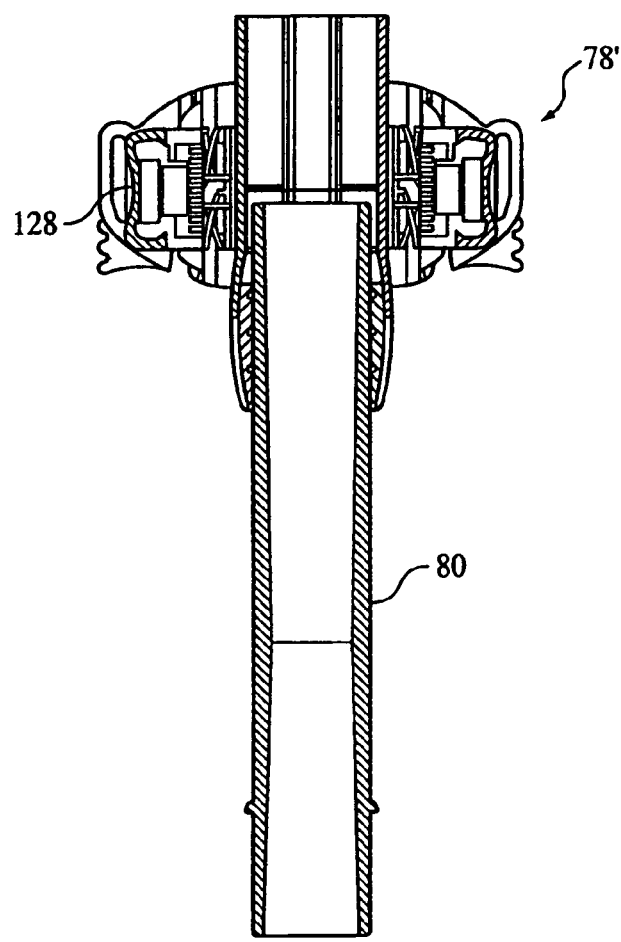
FIG. 21C is a cross-sectional side view of the length adjustment assembly and the angle adjustment assembly of FIG. 21A.
Figure 21D:
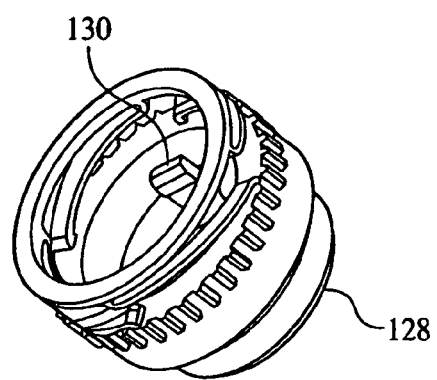
FIG. 21D is a perspective view of the interior of the press and release buttons of the length adjustment assembly and the angle adjustment assembly of FIG. 21A.

In FIGS. 19A and 19B, which illustrate further exemplary embodiments for the formable support, the support is mounted to outer curved surface 40 of nasal cushion 28 using three pockets 59 provided on outer curved surface 40. Each pocket receives an end portion of the formable support. The configurations for attaching the formable support to the nasal cushion shown in FIGS. 3, 4, 18, and 19A-19B provide an advantage in that the formable support can be readily attached and detached from the nasal cushion. This allows formable supports of different stiffness to be used in the same nasal cushion and allows for easy replacement of the nasal cushion or the formable support.

Figure 17A:
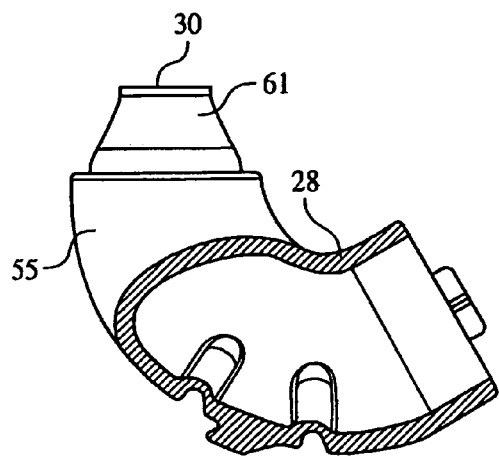
FIGS. 17A and 17B are cross-sectional views and FIG. 17C is a top view of a nasal interface device according to a further embodiment of the present invention.
Figure 17B:
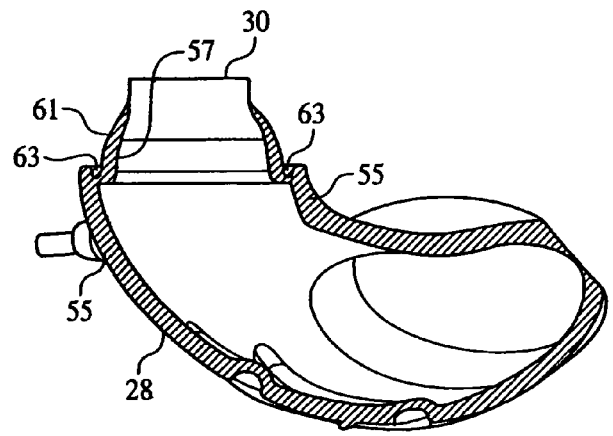
Figure 17C:
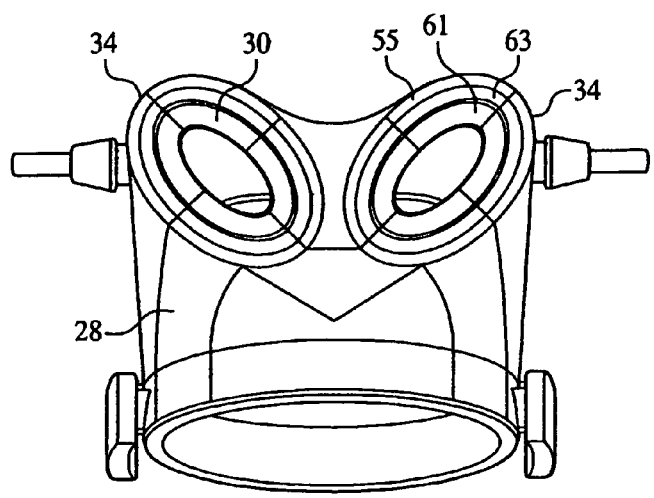

The present invention contemplates varying a property of the walls forming nasal cushion 28, outlet legs 34, and nares elements 30, such as the thickness and/or elasticity, to provide performance improvements in the patient interface, such as increased comfort, better mask/patient seal, and/or greater customization capability. For example, FIGS. 17A-17C illustrates a nasal cushion wall 55 that is relatively thick. A base portion 57 of a nares element wall 61 is also relatively thick, but tapers as the distance from base portion 57 increases. Between the relatively thick walled based portion 57 of nares element wall 61 and nasal cushion wall 55 is a relatively thin wall portion 63. Providing thin wall portion 63 between these two thick walls allows nares element 30 to articulate relative to nasal cushion 28 so that the nares element better fits the nostrils of the user. In addition, the formabilty of the nasal cushion is increased by providing a relatively deep spacing between outlet legs 34. It is to be understood that a similar function, whereby the nares elements are moveable relative the nasal cushion, can be achieved without varying the thickness of the walls. For example, a material having a relatively high degree of elasticity (stretchable) can be provided at location 63, while walls 55 and 61 are formed from a material of lower elasticity. Of course, a combination of varying wall thickness and elasticity are also contemplated by the present invention.

In the illustrated embodiments, with the possible exception of that shown in FIGS. 19A and 19B, stem portion 44 of T-shaped formable support 42 is receivable in a corresponding notched portion 68 provided in oval shaped opening 60 of cradle 58. Alternatively, formable support 42 can be mounted to nasal cushion 28 by corresponding pockets on outer curved surface 40 of nasal cushion 28, as shown in FIGS. 19A and 19B.

In the present invention, oval shaped opening 32 of nasal cushion 28 is coupled to a coupling elbow or cradle 58. Cradle 58 is substantially curved having an oval shaped opening 60 that connects to oval shaped opening 32 of nasal cushion 28. In the illustrated exemplary embodiment, cradle 58 has a double wall construction 62 and forming a hollow chamber 64. An opposite end 66 of the cradle is substantially circular. See FIGS. 3-4. It is to be understood, however, that the present invention contemplates joining nasal cushion 28 and cradle 58 using other configurations for the cooperating parts. For example, a groove (double wall) can be provided in the end of nasal cushion 28 so that the end of cradle 58 fits into the groove formed in the cushion.

In the illustrated embodiment, tabs 67 are provided on opposing sides of nasal cushion 28 at end 66. Corresponding tab receiving slots 69 are provided on cradle 58 for receiving tabs when the nasal cushion is properly coupled to the cradle. Tabs 67 and slots 69 assist in aligning the cushion with the receiving end of the cradle. To help retain cradle 58 and cushion 28 in an engaged relation, tabs 67 and slots 69 are configured and arranged so that the tab cannot be easily pulled apart. For example, in the illustrated embodiment, slot 69 has an "arrow" shape and tab 67 is a similar shape. This "arrow" shape allows the tab to be readily inserted into the slot due to the wedge-shaped tip of the arrow, but prevents disengagement due to the flat back end of the tab abutting the flat back ends of the arrow-shaped slot. Of course, other configurations for tab 67 and slot 69 are provided for accomplishing these functions. In addition, the tab can be provided on the cradle and the slot provided in the cushion.

As shown in FIGS. 4 and 6-8, an outer curved surface 70 of cradle 58 includes an exhaust diffusion plate 72 having diffusion holes 74 for exhausting exhaled gas from the pressurized system to the atmosphere. Preferably, exhaust diffusion plate 72 includes diffusion holes 74 having a tapered diameter and arranged in a fan pattern. In the illustrated embodiment, exhaust diffusion plates 72 provide a substantially 180 degree radial diffusion. It is to be understood that the present invention contemplates forming the diffusion plate at other locations on the cradle and forming the holes in the diffusion plate in any desired configuration to achieve an almost infinite number of different diffusion patterns. For example, multiple diffusion plates can be provided so that diffusion plates are provided at various locations on the cradle. In addition, the holes, which are otherwise provided in the diffusion plate, can be formed directly in the wall of the cradle. In which case, the diffusion plate(s) can be eliminated. Of course, a combination of exhaust ports defined directly in the wall of the patient interface device and a diffusion plate(s) can also be used. Diffusion plate 74 is preferably formed from a rigid material. However, the present invention also contemplates that the diffusion plate can be formed from a material that is deformable.

End 66 of cradle 58 is connected to a length adjustment assembly 76, which adjusts the distance between an angle adjustment assembly 78 and nasal interface device 12, to accommodate patients having different facial sizes. As shown in FIGS. 1-2 and 9-13, length adjustment assembly 76 includes a tubular section 80 and an adjustment nut 82. Tubular section 80 is received within adjustment nut 82. A lower end 84 of tubular section 80 is connected to circular end 66 of cradle 58 using any conventional technique, such as a friction fitting. Threadings 86 are provided on the exterior of tubular section 80 and on an interior of adjustment nut 82. Length adjustment is accomplished by rotating adjustment nut 82 so that the threadings on adjustment nut 82 engage the threadings on tubular section 80. Rotating adjustment nut 82 causes tubular section 80 to move up or down inside a pivot tube 88 coupled to adjustment nut 82. Pivot tube 88 is part of angle adjustment assembly 78, which is described in greater detail below.

Angle adjustment assembly 78, which is best shown in FIGS. 9-13, is a position adjustment mechanism with pre-fixed angular locating positions to control the position or angle of the rigid gas flow conduit relative to the patient's face over a relatively large range of angles, e.g., a 45° range. In addition to this relatively large adjustment capability, angle adjustment assembly provides a force adjustment by means of an integrated spring on a secondary pivoting member over in a narrower range of angles, e.g., 5° range. The angle adjustment assembly allows a cantilevered support to support the patient interface device without a set of headgear straps located at the patient interface device.

Angle adjustment assembly 78 includes an adjustment mechanism that itself includes a mounting bracket 90, an angular pivot housing 92, and a pivot tube 88. Mounting bracket 90 is attached to harness assembly 26 of headgear 22 and comprises a pair of substantially parallel mounting bracket arms 94 extending from a harness assembly attaching portion 96. Each mounting bracket arm 94 is substantially L-shaped and extends outward from harness assembly attaching portion 96 of mounting bracket 90 to a bend portion 98 before extending upwardly to a distal portion 100.

Each distal portion 100 includes a plurality of spaced locking/adjustment key holes 102. In the illustrated embodiment, nine key holes 102 are provided on each distal portion 100 corresponding to nine preset positions, which are about 5 degrees apart covering a total angular range of 45 degrees.

Bend portion 98 of each mounting bracket arm 94 includes a pivot hole 104. A pivot axis 106 extends between pivot holes 104 in mounting bracket arms 94. Both angular pivot housing 92 and pivot tube 88 pivot relative to mounting bracket 90 independently about axis 106. Angular pivot housing 92 is mounted between the mounting bracket arms 94 and includes a substantially circular bracket 108 having an interior annular opening 110 and a pair of substantially parallel extension arms 112 extending from opposite sides of circular bracket 108. Circular bracket 108 has a pair of slots 114 having pivot holes 116 corresponding to mounting bracket pivot holes 104. A distal end 118 of each extension arm 112 includes a rigid oval portion (FIG. 13) or a flat rectangular portion, as shown in FIGS. 11-12, functioning as a thumb rest.

On the exterior portion of each extension arm 112, intermediate circular bracket 108 and distal end 118, there is provided an extension key 120 adapted for locking/adjustment engagement with the plurality of locking/adjustment key holes 102 of corresponding mounting bracket arm 94. The angular position of angular pivot housing 92 relative to mounting bracket 90 is locked by two extension keys 120 on extension arms 112 of angular pivot housing 92. In the illustrated embodiment, the locking is dual directional, but could also be a one-directional ratchet type. The angular position of angular pivot housing 92 relative to mounting bracket 90, and thus, the angular position of patient interface device 12 relative to the forehead of the patient, can be released and adjusted by squeezing and moving the two thumb rests at distal ends 118 of extension arms 112 to move extension keys 120 from one angular position to the next and then releasing the thumb rests so locking/adjustment keys 120 are engaged within the desired locking/adjustment key holes 102. This angular positioning of the angular pivot housing is illustrated by arrow 107 in FIG. 13.

Pivot tube 88 is a rigid tubular member mounted within interior annular opening 110 of circular bracket 108. A pair of pivot projections 122 extend from opposite sides of the exterior of pivot member 88. When assembled, each pivot projection 122 extends through a corresponding circular bracket pivot hole 116 and then through a corresponding mounting bracket arm pivot hole 104. Pivot tube 88 pivots relative to mounting bracket 90, but its motion is restricted by angular pivot housing 92. Pivot tube 88 provides a second range of movement of about 5 degrees.

Figure 11:
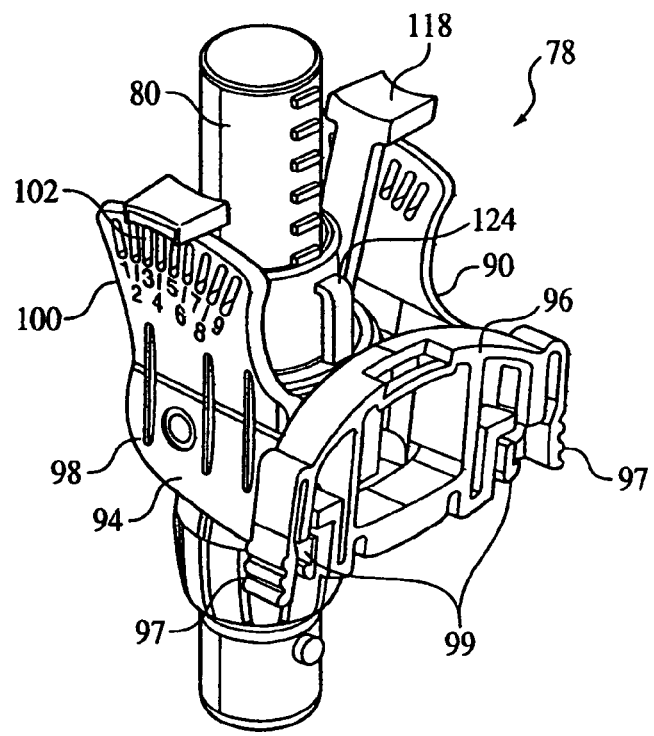
FIG. 11 is a rear perspective view of the length adjustment assembly and the angle adjustment assembly of FIG. 9.
Figure 12:
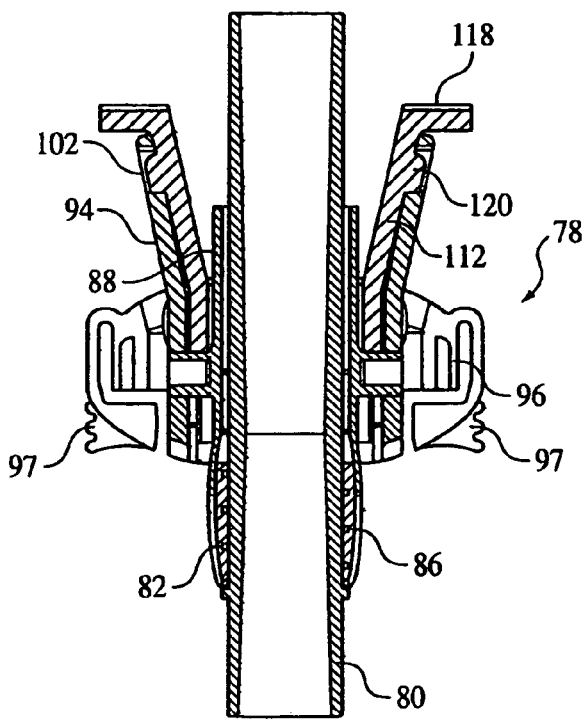
FIG. 12 is a cross-sectional view of the length adjustment assembly and the angle adjustment assembly of FIG. 9.
Figure 13:
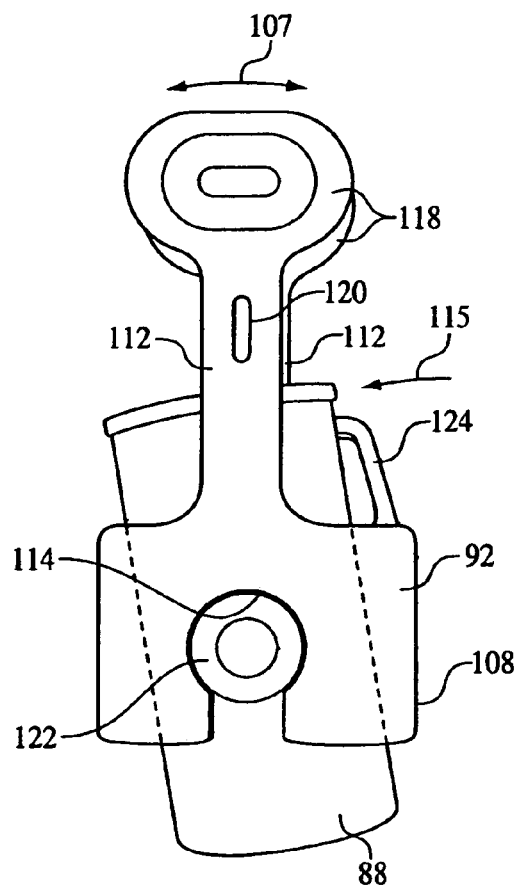
FIG. 13 is a side view of specific components of the angle adjustment assembly.

As shown in FIGS. 11 and 13, pivot tube 88 is biased by an integrated lever spring 124 provided on circular bracket 108 intermediate extension arms 112. The bias provided by the lever spring is illustrated by arrow 115 in FIG. 13. Pivot tube 88 is pushed inwardly (deflected toward the user when in use) to the most inner position with respect to the angular pivot housing 92 by spring 124. Pivoting of pivot tube 88 against the bias force is limited by contact with the integrated lever spring 124.

Figure 24:
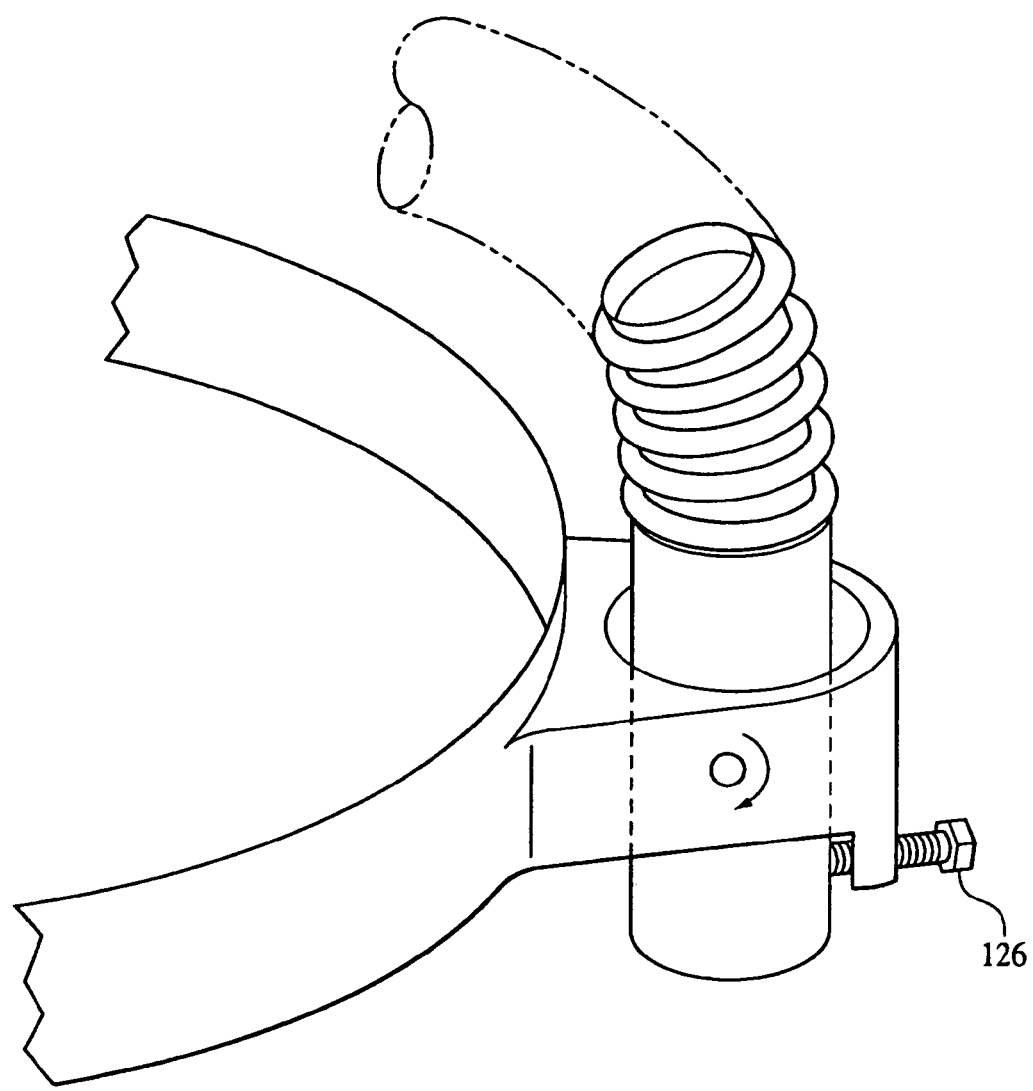
FIG. 24 shows another alternate embodiment of the angle adjustment assembly.

In an alternate embodiment shown in FIG. 24, a thumbscrew 126 is mounted on the front of the pivot tube below the centerline of the pivot. By rotating the screw, the tube is pushed toward the user when donned by the user. Alternatively, the screw could be mounted above the pivot so that rotating the screw causes the tube above the pivot to be pushed out, which, in turn, push the tube below the pivot toward the user. Additionally, a torsion spring could be mounted on the pivots to provide a spring force biasing the position of the patient interface toward the user. Of course, other spring type arrangements can be provided on angle adjustment assembly 78 to bias the patient interface device at end 84 of tube 80 toward the user.

An alternate embodiment of angle adjustment assembly 78' is shown in FIGS. 21A-21D. In this embodiment, angle adjustment assembly 78' includes a pair of press-and-release buttons 128 with a built-in spring 130 action. Press-and-release buttons 128 are operated by pressing the buttons to disengage a locking mechanism, thereby allowing tube 80 to rotate relative to mounting bracket 90' to the desired position.

Figure 20:
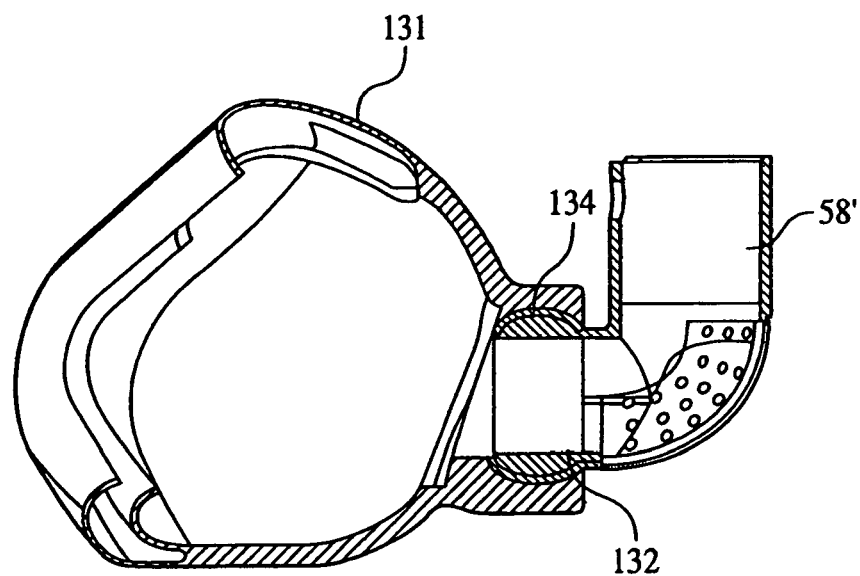
FIG. 20 is a cross-sectional side view of an alternate embodiment having a ball and socket connection.

In a further alternate embodiment, the coupling between the patient interface device and the coupling elbow or cradle is adjustable. An example of this is shown in FIG. 20. More specially, FIG. 20 illustrates a coupling between cradle 58' and a nasal mask 131. This illustrated coupling is a ball 132 and socket 134 type joint, where the ball is allowed to rotate within the socket. More specifically, cradle 58' includes a ball end 132, which is receivable in a socket portion 134 of the patient interface device, thereby allowing the tubing portion to be angled or rotated with respect to the patient interface device. Friction between the ball and socket maintain the position between these two elements once they are moved to the desired position. Although a ball-and-socket type of configuration is shown, it is to be understood that other adjustable type joints could be used for coupling the patient interface device to the elbow/cradle. In addition, the ball-and-socket arrangement can be reversed, with the ball being provided on the patient interface and the socket on the elbow/cradle.

As shown in FIGS. 1, 2, and 14-16, harness assembly 26 of headgear 22 is adapted to be worn on the head of a patient and includes a cross strap 136 extending over the top of the patient's head and a forehead strap 138 extending over the forehead and temples of the patient. Forehead strap 138 and cross strap 136 are formed from a semi-rigid plastic and preferably have a cushioning element on the patient contacting side. Each end 140 of forehead strap 138 includes an angled connecting port 142 for adjustable connection to cross strap 136. In the illustrated embodiment, each angled connecting portion 142 includes five adjusting holes 144, while each end of the cross strap 136 includes two corresponding projections 146 enabling the corresponding connecting portion 142 of forehead strap 138 and the ends of cross strap 136 to be selectively interconnected to adjustable lengths depending on the head parameters of the patient to provide a secure fit. It can be appreciated that each side of cross strap 136 can be adjusted independently of the other side. In addition, the hole and projections can be reversed, and more or less holes and projections can be provided.

Harness assembly attaching portion 96 of mounting bracket 90 is attached to a center portion of forehead strap 138. In an exemplary embodiment of the present invention, harness assembly attaching portion 96 is releaseably attached to a mounting bracket 166 provided on forehead strap 138. See FIGS. 14-16.

A rear strap 148 is provided having a rigid connecting element 150 on each end. Each connecting element 150 is receivable in a key slot opening 152 provided on angled connecting portion 142 below the cross strap adjusting holes 144. Rear strap 146 loops through connecting elements 150 and is adjusted by hook and loop fasteners or other appropriate means. Thus, each end of rear strap 146 is selectively attachable to the semi-rigid headgear portions and the length of the rear strap is adjustable on either end. Those skilled in the art will appreciate that the connecting element 150 and slot 152 arrangement can be reversed, with the slot or other female receiving portion provided on the rear strap and the connecting element and the other cooperating male portion provided on angled connecting portion 142.

Figure 25:
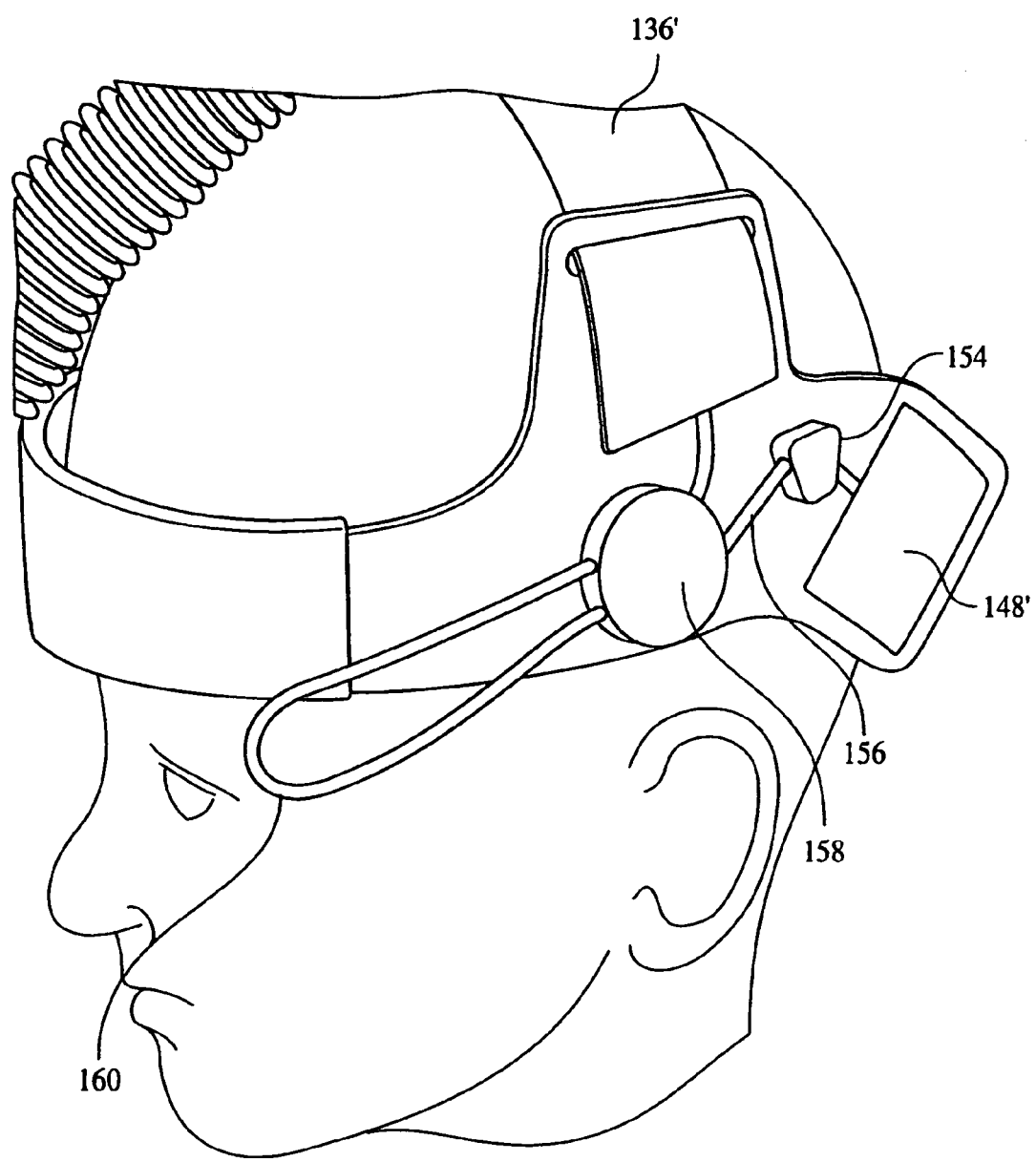
FIG. 25 shows another alternate embodiment of the headgear adjustment assembly for adjusting the fit of the headgear.

Alternatively, as shown in FIG. 25, adjustment of harness assembly 26 is accomplished by means of an adjustment assembly 154, which simultaneously adjusts both cross strap 136' and rear strap 148'. Specifically, cross strap 136' and rear strap 148' are linked together on one side of harness assembly 26 via a connecting element 156, such as a cord. Connecting element 156 is attached to adjacent ends of cross 136' and rear 148' straps. Connecting element 156 is threaded through a locking element 158 forming a loop 160. The effective length of cross strap 136' and rear strap 148' is adjusted by adjusting the size of the connecting element loop 160 through locking element 158. Thus, the positions of cross strap 136' and rear strap 148' about the patient's head are simultaneously adjusted by the single adjustment of the connecting element 156.

It should be noted that the present invention contemplates eliminating loop 160 in favor of allowing cross strap 136' and rear strap 148' to be adjusted independently. That is, separate connecting elements can be provided for cross strap 136' and rear strap 148' so that each can be adjusted by means of locking element 158.

Figure 23:
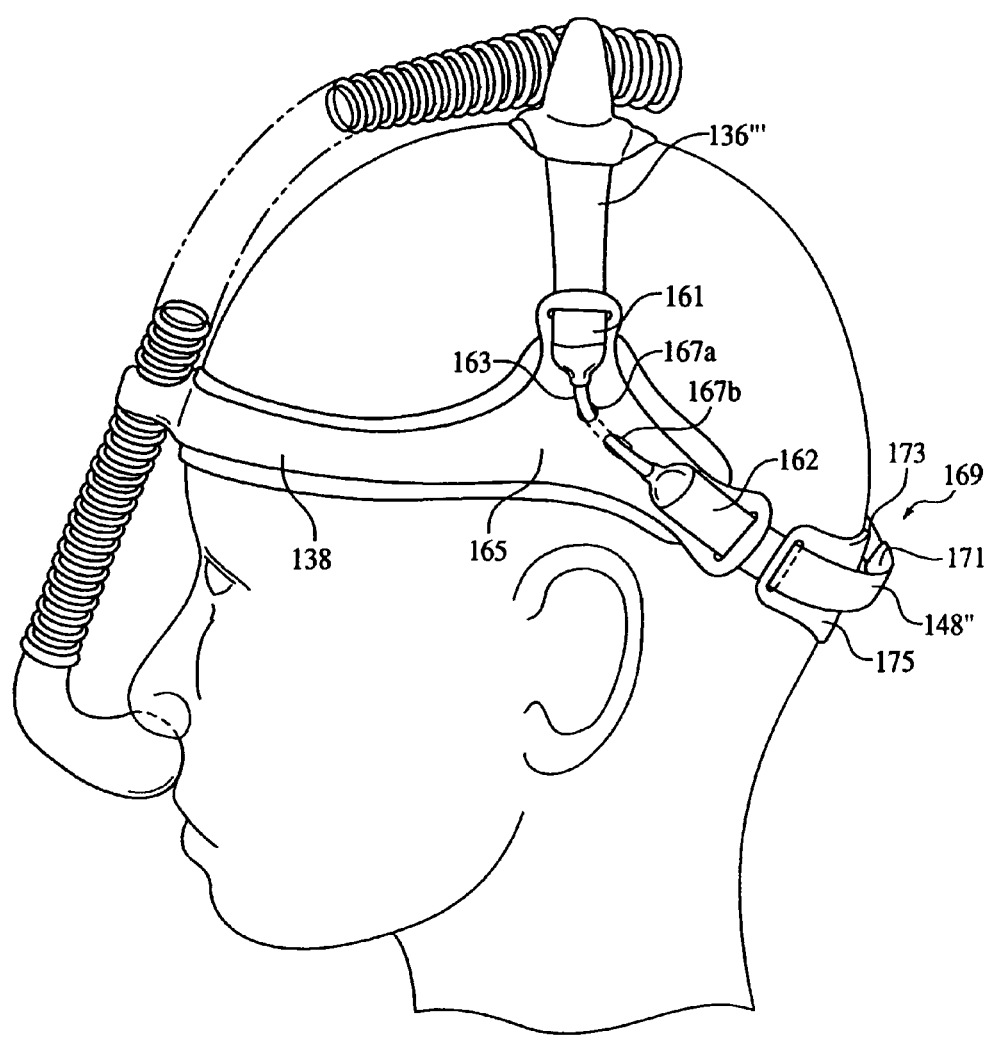
FIG. 23 is a side view of an alternate embodiment of the headgear assembly according to the principles of the present invention.

FIG. 23 illustrates a further embodiment for controlling the adjustment of the harness assembly. In this embodiment, end portions 161 and 162 of cross strap 136''' and rear strap 148''', respectively, are connected to one another via a connecting member 163. In the illustrated embodiment, connecting member 163 is a cord that is connected to portion 165 of the headgear assembly. More specifically, connecting member 163 runs through holes 167a, 167b provided in portion 165. Cross strap 136'', rear strap 148'', or both, include a strap tightening system 169, which in the illustrated embodiment is shown as being provided on rear strap 148''.

Strap tightening system 169 is any conventional system that is used to increase or decrease the lengh of the strap, such as a hook and loop configuration. In the illustrated exemplary embodiment, hooks 171 are provided on strap 148'' and corresponding loops 173 are provided on a pad 175. Of course, this configuration can be reversed. Tightening of strap 148'' is accomplished by pulling more of the strap across the pad and fastening the strap back onto the pad.

Because of the connection between cross strap 136'' and rear strap 148'' provided by connecting member 163, tightening or shortening the length of one of these straps has the effect of simultaneously tightening or shortening the length of the other. Thus, this embodiment for the headgear provides a single means (strap tightening system 169) for adjusting the one strap that automatically adjusts another strap in the headgear.

Referring again to FIGS. 1, 2, and 14-16, the upper end of tubular section 80 of length adjustment assembly 76 is connected to an air hose 164. Cross strap 136 further includes mounting bracket 166 for mounting a crown swivel 168 for attaching air hose 164 to conduit 16. Crown swivel 168 includes a lower tubular member 170 and an upper tubular member 172 each connected to a swivel joint 174, so that the lower tubular member 170 and the upper tubular member 172 can freely swivel. The lower tubular member 170 includes a clip portion 176 for selectively and releasably connecting mounting bracket 166 to cross strap 136. In an exemplary embodiment of the present invention, clip portion 176 selectively connects mounting bracket to strap 136 in the same manner as harness assembly attaching portion 96 attaches to forehead strap 138 discussed below.

Figure 14:
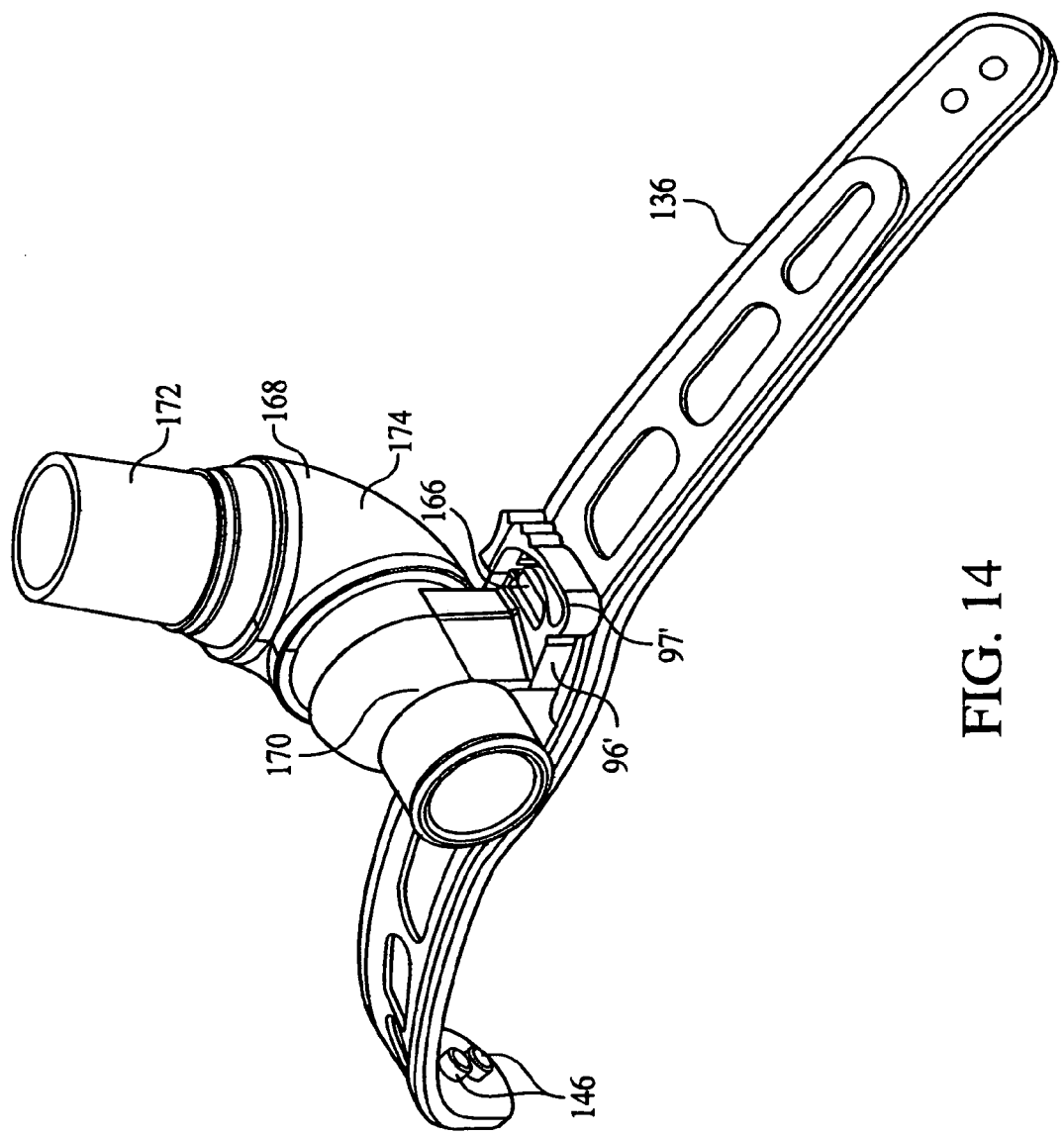
FIGS. 14-16 are perspective, front (partially in section), and top views, respectively, of the headgear and a mounting assembly in the patient interface assembly of FIG.1.
Figure 15:
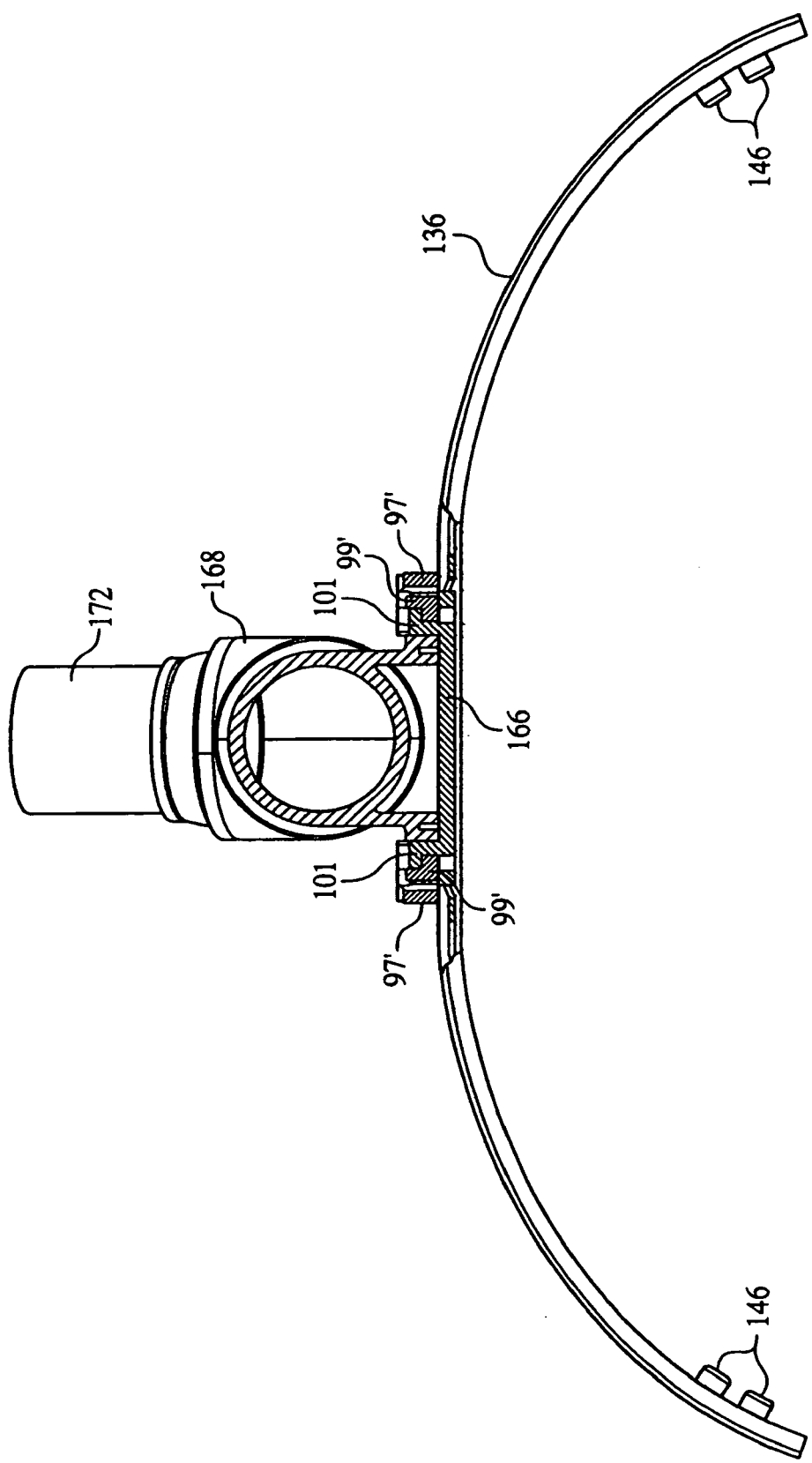
Figure 16:
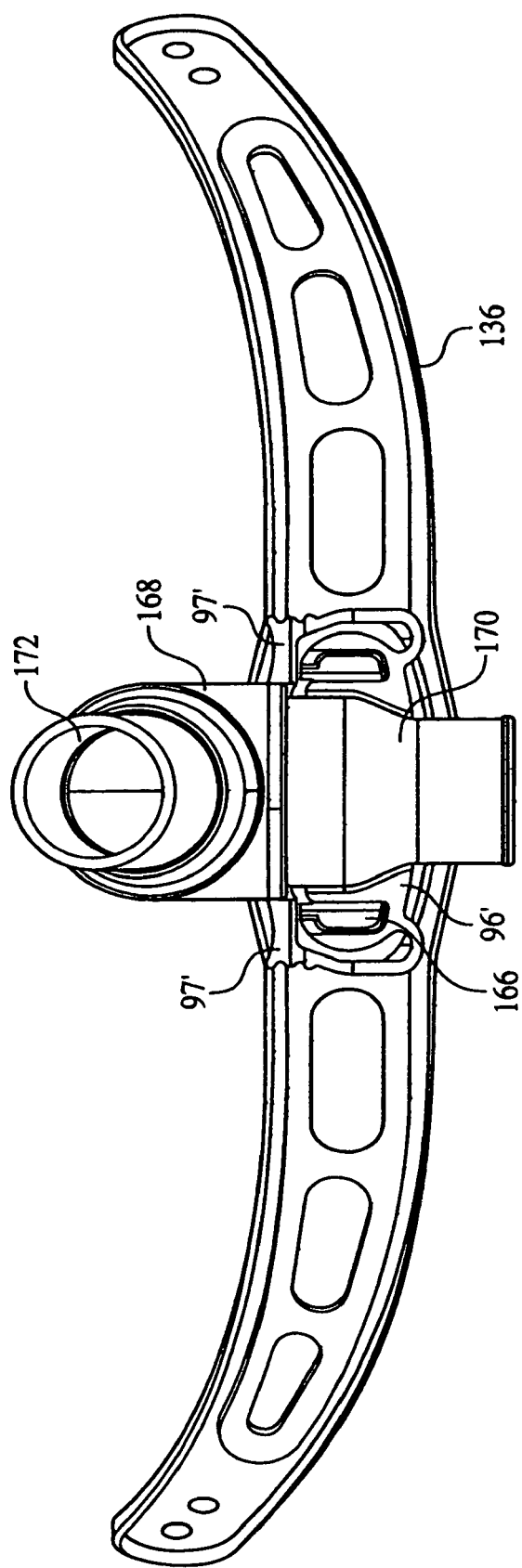

Referring now to FIGS. 11, 12, and 14-16, the manner in which harness assembly attaching portion 96 attaches to forehead strap 138 and lower tubular member 170 attaches to cross strap 136 will now be discussed. It should be noted that the manner in which assembly attaching portion 96 is attached to forehead strap 138 and the manner in which an attaching portion 96' disposed on lower tubular member 170 is attached to cross strap 136 are substantially similar. Thus, reference is made only to one of these attachment configurations, namely the attachment of attachment portion 96' on lower tubular member 170 to cross strap 136, and only this attachment configuration is shown in FIGS. 14-16.

Cross strap 136 and forehead strap 138 each includes a mounting bracket 166 on which the corresponding attaching portion 97, 97' attaches. Please note that only the mounting bracket on the cross strap is shown. Each attaching portion 96, 96'; includes clip portions 97, 97' on each side of attaching portion 96, 96'. Squeezing clip portions 97, 97' toward one another causes them to deflect from a biased position, where an engaging portion 99, 99' engages a portion 101 of mounting bracket 166, to a deflected position, where engaging portion 99, 99' disengages from portion 101, thereby allowing the attaching portion to slide off of the mounting bracket. See FIGS. 11 and 12.

Preferably, mounting bracket 166 and attaching portion 96, 96' are configured such that they can only be assembled in one orientation to ensure that the patient interface assembly is assembled correctly. The ability to attach and detach mounting assembly 28 and angle adjustment assembly 78 from the corresponding portion of the headgear assembly allows the components of the patient interface assembly to be disassembled for easy cleaning and allows for easy part replacement.

Figure 22A:
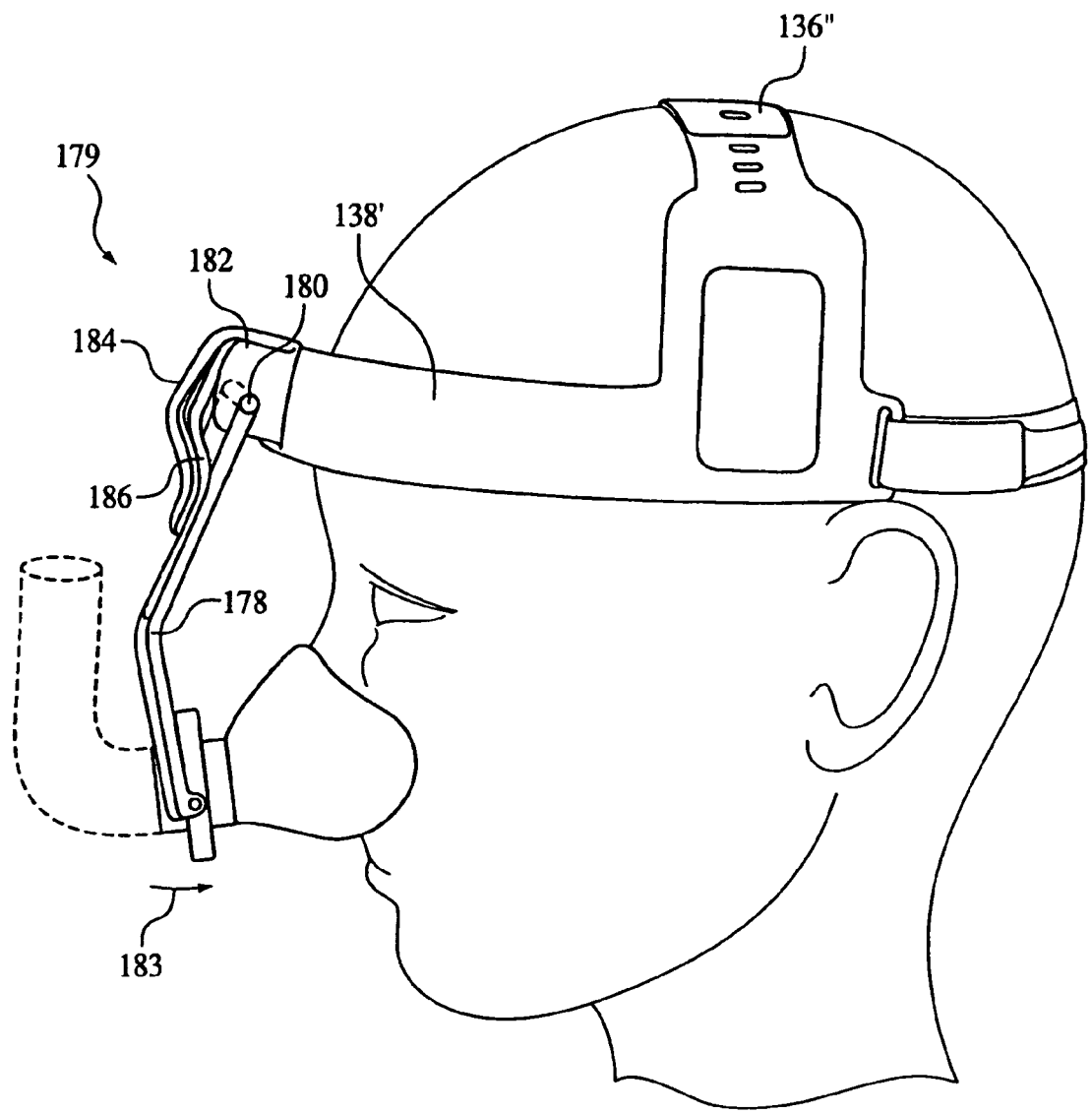
FIGS. 22A and 22B are side and perspective views, respectively, of an alternate embodiment of the patient interface assembly of the present invention shown being worn by a patient.
Figure 22B:
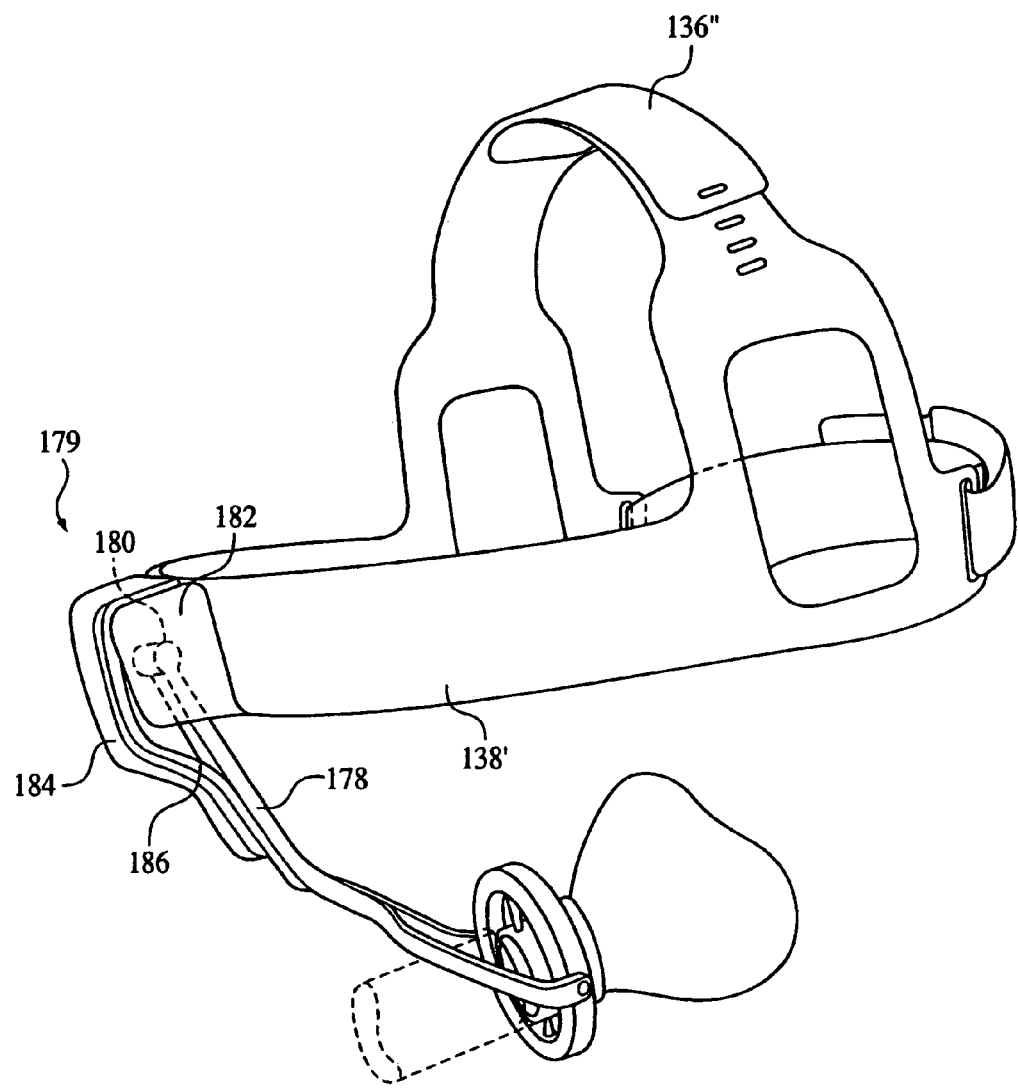
Figure 22C:
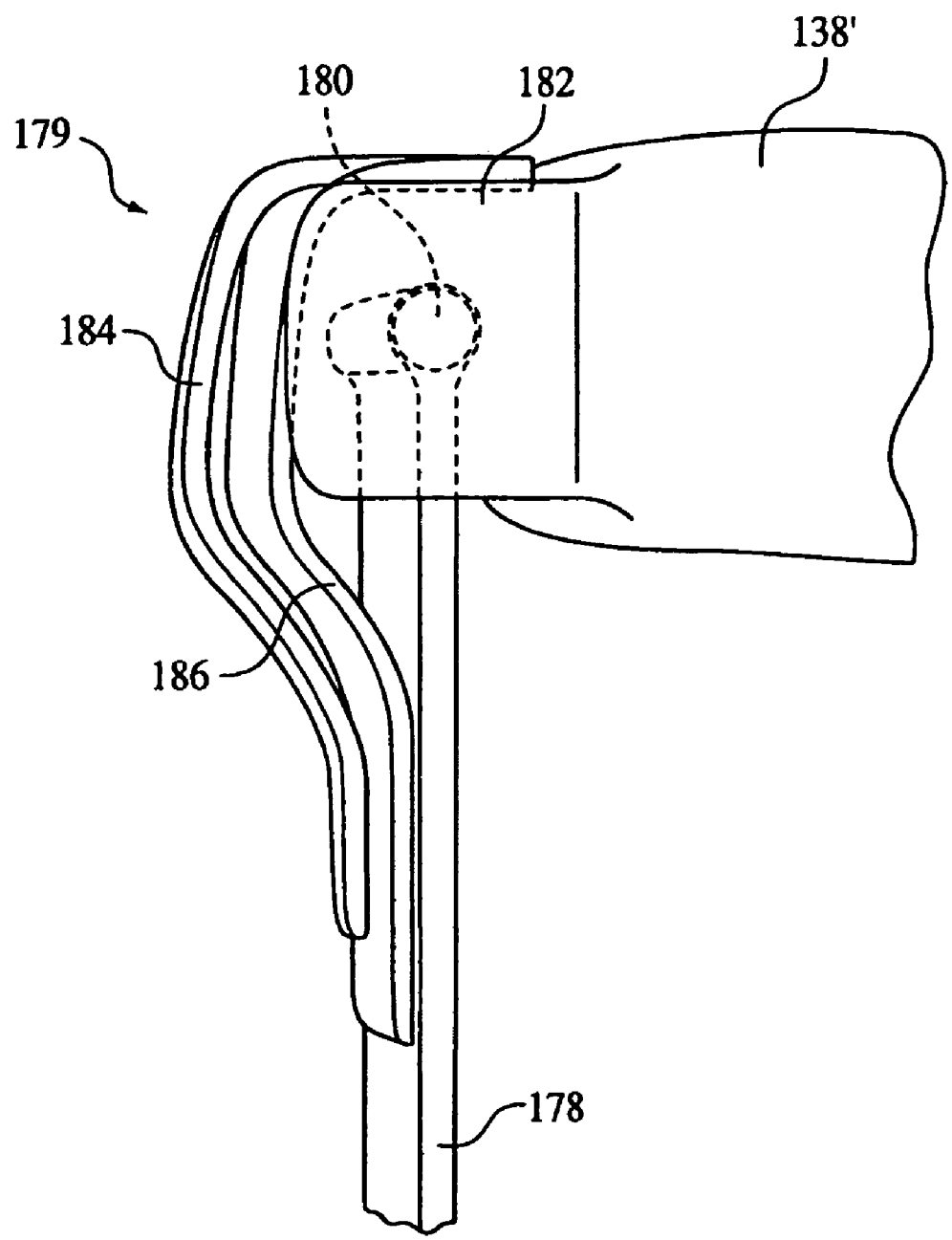
FIG. 22C is a detailed view of the angle adjustment assembly of FIG. 22A.

A still further alternate embodiment is shown in FIGS. 22A-22C. In this embodiment, there is no length adjustment assembly 76, but there is a biasing assembly, generally indicated at 179, for the patient interface device, which in this embodiment, is a nasal mask. The nasal mask is attached to one end of a lever bar 178. The opposite end of the lever bar is connected to a pivot 180 on a mounting bracket 182 located at the central portion of the forehead strap. An integrated spring 184 is provided on the mounting bracket to bias the patient interface device toward the user when the patient interface system is donned by the user, as indicated by arrow 183. Spring 184 may be fixed or adjustable to allow an increasing or decreasing sealing force. This adjustment would typically be made based on the patient's individual prescription pressure. In the illustrated embodiment, a second spring 186 is provided on mounting bracket 182 to provide an additional bias force on lever bar 178. Of course, this second spring is optional.

It is also to be understood that the present invention contemplates that other spring biasing techniques, in place or on in addition to those shown in the figures, can be used to urge the patient interface device toward the patient. For example, a spring can be provided on the patient side of level bar 178 and attached to mounting bracket 182 or the forehead strap.

Figure 26:
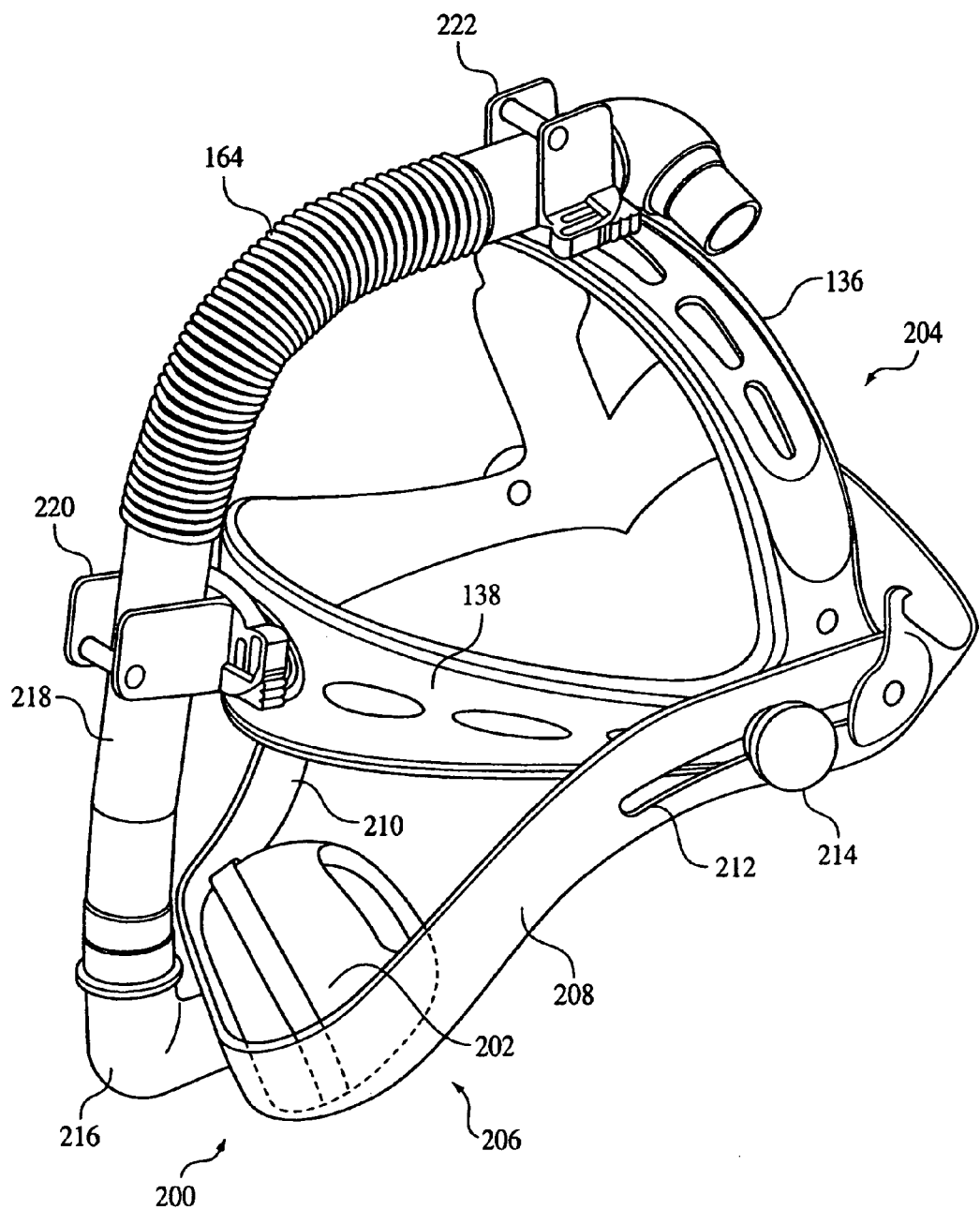
FIG. 26 is a perspective view of a still further embodiment of a patient interface assembly according to the principles of the present invention.
Figure 27:
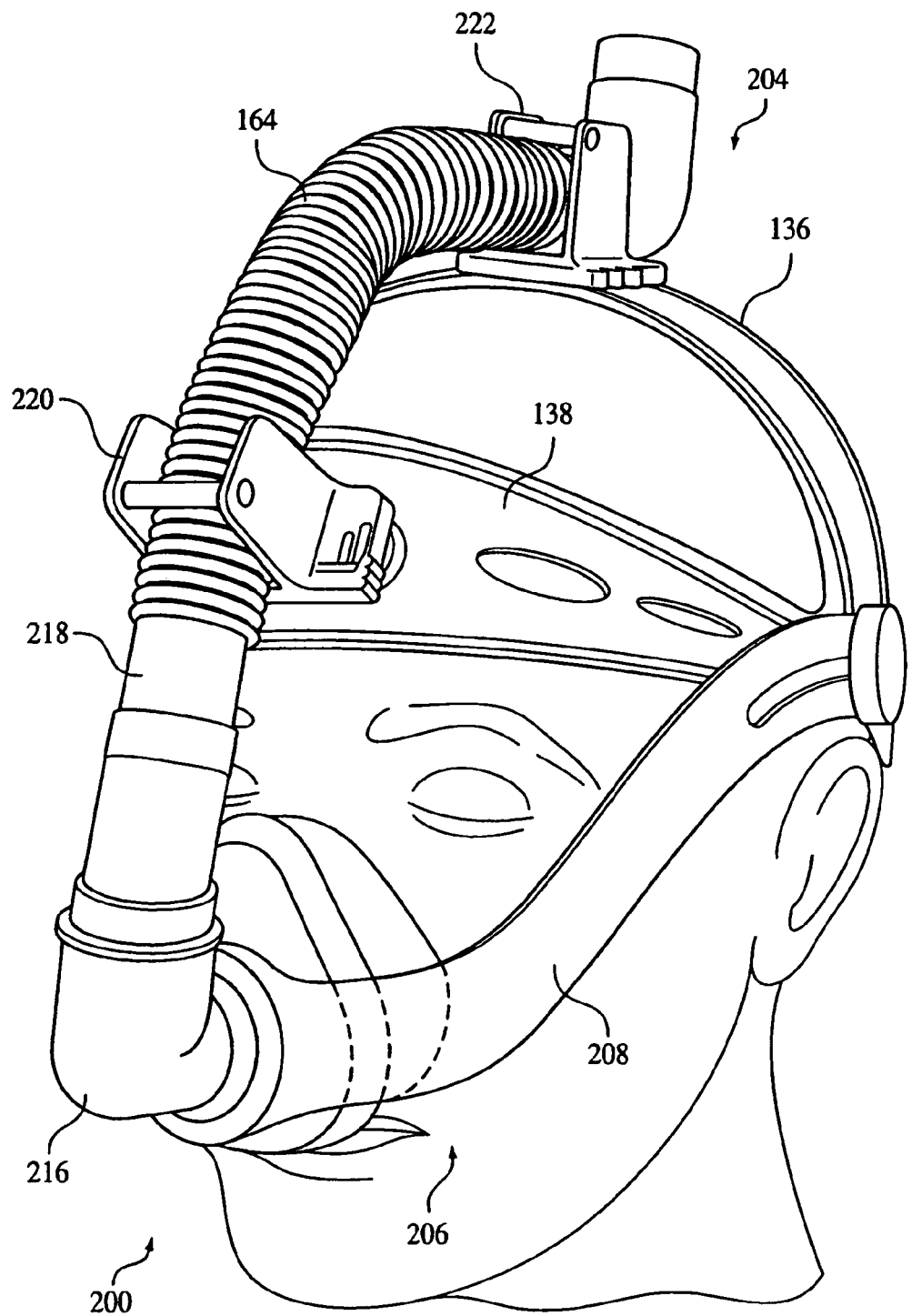
FIG. 27 is a perspective view of the patient interface assembly of FIG. 26 shown being worn by a patient.

FIGS. 26 and 27 illustrate another embodiment of a patient interface assembly 200 according to the principles of the present invention, in which FIG. 27 shows the patient interface assembly as worn by a patient. Patient interface assembly 200 includes a patient interface device 202 and a headgear 204 adapted to be worn by the patient. In the illustrated embodiment, patient interface device 202 is a nasal mask adapted to cover the area of the face surrounding the nares. It is be understood that the patient interface device can correspond to any conventional interface device or the interface device 12 discussed above. Headgear 204 corresponds to headgear 22 discussed above and can include all of the features of that headgear.

One difference between the patient interface assembly of FIGS. 26 and 27 and that of the previous embodiment is in the manner in which the patient interface device is biased or held against the surface of the patient. In the embodiment of FIGS. 26 and 27 a rigid coupling member, generally indicated at 206, couples patient interface device 202 to headgear 204. The rigid coupling member includes a first arm 208 connected between a first side of the patient interface device and a first side of the headgear, and a second arm 210 connected between a second side of the patient interface device and a second side of the headgear, wherein the first and the second arm are rigid. The first and second arms are preferably formed from a light-weight material, such as plastic. In addition, the first arm and the second arm are also preferably sized and shaped that they generally match the contour of a human face that underlies each arm when the patient interface assembly is donned by the patient.

In a preferred exemplary embodiment of the present invention, the first arm and the second arm are adjustably coupled to the headgear such that the length of the first and second arms can be controlled to fit the needs of each patient. In the illustrated embodiment, this adjustable connection is achieved by providing a slot 212 in the end of first arm 208 and at the end of the second arm. Of course, only the first arm is shown in FIGS. 26 and 27. A friction lock 214 is disposed in the slot. The friction lock includes a post that is disposed in the slot and a lock nut that is threaded onto the post. Loosening the nut allows the post to move along the slot, and tightening the nut causes the nut to hold the friction lock in place. It is to be understood that the present invention contemplates using any conventional technique for controlling the positions of the first and second arms relative to the headgear.

The first and second arms can be connected to the patient interface device in a fixed relationship, i.e., such that the arms do not move relative to the mask shell, or in a non-fixed relationship. In an exemplary embodiment, the non-fixed relationship includes coupling the arms to an elbow connector 216 such that the arms swivel or rotate about this connector. For example, the present invention contemplates that the first and second arms are defined from an integral piece of material with a hole defined therein. The elbow coupling is disposed in the hole such that the arms can rotate around the elbow coupling.

As in the previous embodiment, a connector tube 218 is connected to elbow coupling 216 and an air hose 164 is coupled to tube 218. A connecting element 220 is provided to couple air hose 164 and/or coupling tube 218 to a forehead strap 138. If desired, another coupling element 222 can be provided at cross strap 136 to connect the patient circuit to the headgear. Connecting elements 220 and 222 can be any conventional device that secures the tube to the headgear, such as a simple strap, or they can correspond to the coupling systems discussed above.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient interface assembly for use in the delivery of a breathing gas to a patient, comprising:
   (a) a patient interface device;
   (b) a headgear adapted to be worn by a patient; and
   (c) a coupling member adapted to couple the patient interface device to the headgear, wherein the patient interface device is pivotally connected to the headgear via the coupling member, and wherein the coupling member includes an angle adjustment assembly for adjusting an angle of the patient interface device relative to such a patient, the angle adjustment assembly comprising:
   (1) a mounting bracket adapted to be mounted to the headgear,
   (2) an angular pivot housing, and
   (3) a pivot tube mounted within the angular pivot housing, wherein the mounting bracket, angular pivot housing, and the pivot tube are pivotable about a common axis.

2. The patient interface assembly of claim 1, wherein the mounting bracket has mounting bracket arms each having locking elements corresponding to preset angular positions, and the angular pivot housing comprises extension arms having a locking element for mating with the locking elements on the mounting bracket arms.

3. The patient interface assembly of claim 1, wherein the patient interface device comprises a nasal cushion and a nares element.

4. The patient interface assembly of claim 1, further comprising a cradle coupling the patient interface device to the coupling member.

5. The patient interface assembly of claim 4, further comprising an exhaust diffusion plate mounted on the cradle.

6. The patient interface assembly of claim 1, wherein the headgear comprises:
   a cross strap adapted to extend over the top of a patient's head;
   a forehead strap adapted to extend over the forehead and temples of such a patient; and
   a rear strap adapted to extend about the rear portion of such a patient's head.

7. The patient interface assembly of claim 2, wherein the cross strap, the forehead strap, and the rear strap are connected to each other by an adjustment assembly.

8. The patient interface assembly of claim 7, wherein the adjustment assembly provides simultaneous adjustment of both the cross strap and the rear strap.

9. The patient interface assembly of claim 1, wherein the coupling member includes a length adjustment assembly for adjusting a distance between the coupling member and the patient interface device.

10. The patient interface assembly of claim 1, further comprising a spring associated with the coupling member and adapted to bias the patient interface device against such a patient's face responsive to the patient interface assembly being donned by such a patient.

* * * * *